(12) United States Patent
Oliver et al.

US008278047B2

(10) Patent No.: US 8,278,047 B2
(45) Date of Patent: Oct. 2, 2012

(54) BIOPOLYMER SEQUENCING BY HYBRIDIZATION OF PROBES TO FORM TERNARY COMPLEXES AND VARIABLE RANGE ALIGNMENT

(75) Inventors: John Oliver, Bristol, RI (US); Barrett Bready, Providence, RI (US); Peter Goldstein, Providence, RI (US); Franco Preparata, Providence, RI (US)

(73) Assignee: Nabsys, Inc., Providence, RI (US)

( * ) Notice: Subject to any disclaimer, the term of this patent is extended or adjusted under 35 U.S.C. 154(b) by 974 days.

(21) Appl. No.: 12/243,451

(22) Filed: Oct. 1, 2008

(65) Prior Publication Data

US 2009/0099786 A1  Apr. 16, 2009

Related U.S. Application Data

(60) Provisional application No. 60/976,714, filed on Oct. 1, 2007, provisional application No. 60/976,739, filed on Oct. 1, 2007.

(51) Int. Cl.
*C07H 21/00* (2006.01)
*C12Q 1/68* (2006.01)

(52) U.S. Cl. ...... 435/6.11; 435/6.1; 536/23.1; 536/24.3; 977/704

(58) Field of Classification Search .................. None
See application file for complete search history.

(56) References Cited

U.S. PATENT DOCUMENTS

| | | | |
|---|---|---|---|
| 5,314,829 A | 5/1994 | Coles | |
| 5,405,519 A | 4/1995 | Schwartz | |
| 5,427,663 A | 6/1995 | Austin et al. | |
| 5,539,082 A | 7/1996 | Nielsen et al. | |
| 5,560,811 A | 10/1996 | Briggs et al. | |
| 5,599,664 A | 2/1997 | Schwartz | |
| 5,681,947 A | 10/1997 | Bergstrom et al. | |
| 5,683,881 A | 11/1997 | Skiena | |
| 5,720,928 A | 2/1998 | Schwartz | |
| 5,773,571 A | 6/1998 | Nielsen et al. | |
| 5,795,782 A | 8/1998 | Church et al. | |
| 5,837,115 A | 11/1998 | Austin et al. | |
| 5,908,745 A | 6/1999 | Mirzabekov et al. | |
| 5,972,619 A | 10/1999 | Drmanac et al. | |
| 6,015,714 A | 1/2000 | Baldarelli et al. | |
| 6,020,599 A | 2/2000 | Yeo | |
| 6,025,891 A | 2/2000 | Kim | |
| 6,084,648 A | 7/2000 | Yeo | |
| 6,100,949 A | 8/2000 | Kim | |
| 6,108,666 A | 8/2000 | Floratos et al. | |
| 6,128,051 A | 10/2000 | Kim et al. | |
| 6,147,198 A | 11/2000 | Schwartz | |
| 6,150,089 A | 11/2000 | Schwartz | |
| 6,174,671 B1 | 1/2001 | Anantharaman et al. | |
| 6,182,733 B1 | 2/2001 | McReynolds | |
| 6,210,891 B1 | 4/2001 | Nyren et al. | |
| 6,210,896 B1 | 4/2001 | Chan | |
| 6,258,568 B1 | 7/2001 | Nyren | |
| 6,263,286 B1 | 7/2001 | Gilmanshin et al. | |
| 6,267,872 B1 | 7/2001 | Akeson et al. | |
| 6,274,320 B1 | 8/2001 | Rothberg et al. | |
| 6,294,136 B1 | 9/2001 | Schwartz | |
| 6,303,288 B1 | 10/2001 | Furcht et al. | |
| 6,304,318 B1 | 10/2001 | Matsumoto et al. | |
| 6,340,567 B1 | 1/2002 | Schwartz et al. | |
| 6,355,420 B1 | 3/2002 | Chan | |
| 6,362,002 B1 | 3/2002 | Denison et al. | |
| 6,392,719 B2 | 5/2002 | Kim | |
| 6,400,425 B1 | 6/2002 | Kim et al. | |
| 6,403,311 B1 | 6/2002 | Chan | |
| 6,413,792 B1 | 7/2002 | Sauer et al. | |
| 6,428,959 B1 | 8/2002 | Deamer | |
| 6,448,012 B1 | 9/2002 | Schwartz | |
| 6,464,842 B1 | 10/2002 | Golovchenko et al. | |
| 6,503,409 B1 | 1/2003 | Fleming | |
| 6,509,158 B1 | 1/2003 | Schwartz | |
| 6,537,755 B1 | 3/2003 | Drmanac | |
| 6,537,765 B2 | 3/2003 | Stricker-Kongra et al. | |
| 6,610,256 B2 | 8/2003 | Schwartz | |
| 6,617,113 B2 | 9/2003 | Deamer | |
| 6,627,067 B1 | 9/2003 | Branton et al. | |
| 6,672,067 B2 | 1/2004 | Farmer et al. | |
| 6,673,615 B2 | 1/2004 | Denison et al. | |
| 6,685,841 B2 | 2/2004 | Lopez et al. | |
| 6,689,563 B2 | 2/2004 | Preparata et al. | |
| 6,696,022 B1 | 2/2004 | Chan et al. | |
| 6,713,263 B2 | 3/2004 | Schwartz | |
| 6,746,594 B2 | 6/2004 | Akeson et al. | |
| 6,762,059 B2 | 7/2004 | Chan et al. | |
| 6,772,070 B2 | 8/2004 | Gilmanshin et al. | |

(Continued)

FOREIGN PATENT DOCUMENTS

DE  19936302  2/2001

(Continued)

OTHER PUBLICATIONS

Ghosh et al. (Molecular Biosystems (2006) vol. 2, pp. 551-560).*
Bennett et al. Pharmacogenomics (2005) 6:373-382.
Gershow, M., et al., (2007) "Recapturing and Trapping Single Molecules with a Solid-State Nanopore." Nature Nanotech. 2:775-779.
International Search Report and Written Opinion dated May 2, 2009, PCTUS2008/078432.
Ju et al., Proc. Nat. Acad. Sci. USA (2006) 103:19635-19640.
Kasianowicz et al., "Characterization of Individual Polynucleotide Molecules Using a Membrane Channel." Proc. Nat. Acad. Sci. USA 93:13770-13773 (1996).
Margulies et al., (2005) Nature, 437:376-380.
de Pablo, P.J., et al., (2000) "Absence of dc-Conductivity." Phys. Rev. Lett. 85:4992-4995.
Quake et al. Proc. Nat. Acad. Sci. USA (2003) 100:3960-3964.
Riehn, R. et al., (2005) Proc. Nat. Acad. Sci., 102:1012.
Giehart B., et al., (2008) "Nanopore with transverse nanoelectrodes for electrical characterization and sequencing of DNA" Sensors and Actuators B., Elsevier Sequoia S.A, ScienceDirect,132:2.
International Search Report and Written Opinion dated Jun. 29, 2010, PCT/US09/055876, 13 pages.

(Continued)

*Primary Examiner* — Lori A Clow
(74) *Attorney, Agent, or Firm* — Goodwin Procter LLP

(57) ABSTRACT

Methods for sequencing a biopolymer by forming local ternary complexes along the length of the double-stranded biopolymer target molecule using one or more probes and obtaining information about the location of the probe(s) using a detector. These methods offer particular advantage when implemented with nanopore (including micropore) detection systems.

33 Claims, 9 Drawing Sheets

U.S. PATENT DOCUMENTS

| | | |
|---|---|---|
| 6,790,671 B1 | 9/2004 | Austin et al. |
| 6,818,395 B1 | 11/2004 | Quake et al. |
| 6,911,345 B2 | 6/2005 | Quake et al. |
| 6,919,002 B2 | 7/2005 | Chopra |
| 6,927,065 B2 | 8/2005 | Chan et al. |
| 6,936,433 B2 | 8/2005 | Akeson et al. |
| 7,001,792 B2 | 2/2006 | Sauer et al. |
| 7,005,264 B2 | 2/2006 | Su et al. |
| 7,034,143 B1 | 4/2006 | Preparata et al. |
| 7,071,324 B2 | 7/2006 | Preparata et al. |
| 7,118,657 B2 * | 10/2006 | Golovchenko et al. .... 204/192.3 |
| 7,170,050 B2 | 1/2007 | Turner et al. |
| 7,176,007 B2 | 2/2007 | Cox et al. |
| 7,189,503 B2 | 3/2007 | Akeson et al. |
| 7,211,414 B2 | 5/2007 | Hardin et al. |
| 7,217,562 B2 | 5/2007 | Cao et al. |
| 7,238,485 B2 | 7/2007 | Akeson et al. |
| 7,248,771 B2 | 7/2007 | Schmidt et al. |
| 7,250,115 B2 | 7/2007 | Barth |
| 7,262,859 B2 | 8/2007 | Larson et al. |
| 7,279,337 B2 | 10/2007 | Zhu |
| 7,282,130 B2 | 10/2007 | Flory |
| 7,282,330 B2 | 10/2007 | Zhao et al. |
| 7,297,518 B2 | 11/2007 | Quake et al. |
| 7,302,146 B2 | 11/2007 | Turner et al. |
| 7,315,019 B2 | 1/2008 | Turner et al. |
| 7,329,492 B2 | 2/2008 | Hardin et al. |
| 7,351,538 B2 | 4/2008 | Fuchs et al. |
| 7,355,216 B2 | 4/2008 | Yang et al. |
| 7,371,520 B2 | 5/2008 | Zhao et al. |
| 7,402,422 B2 | 7/2008 | Fuchs et al. |
| 7,462,449 B2 | 12/2008 | Quake |
| 7,476,503 B2 | 1/2009 | Turner et al. |
| 7,476,504 B2 | 1/2009 | Turner |
| 7,501,245 B2 | 3/2009 | Quake et al. |
| 7,595,160 B2 | 9/2009 | White et al. |
| 7,678,562 B2 | 3/2010 | Ling |
| 2001/0004728 A1 | 6/2001 | Preparata et al. |
| 2002/0028458 A1 | 3/2002 | Lexow |
| 2002/0058279 A1 | 5/2002 | Fritsch et al. |
| 2002/0127855 A1 | 9/2002 | Sauer et al. |
| 2002/0137089 A1 | 9/2002 | Deamer |
| 2003/0003609 A1 | 1/2003 | Sauer et al. |
| 2003/0064095 A1 | 4/2003 | Martin et al. |
| 2003/0064382 A1 | 4/2003 | Preparata et al. |
| 2003/0080042 A1 | 5/2003 | Barth et al. |
| 2003/0104428 A1 | 6/2003 | Branton et al. |
| 2003/0143614 A1 | 7/2003 | Drmanac |
| 2003/0207326 A1 | 11/2003 | Su et al. |
| 2003/0211502 A1 | 11/2003 | Sauer et al. |
| 2003/0232346 A1 | 12/2003 | Su |
| 2004/0137734 A1 | 7/2004 | Chou et al. |
| 2004/0146430 A1 | 7/2004 | Dugas |
| 2004/0197843 A1 | 10/2004 | Chou et al. |
| 2005/0019784 A1 | 1/2005 | Su et al. |
| 2005/0127035 A1 | 6/2005 | Ling |
| 2006/0019247 A1 | 1/2006 | Su et al. |
| 2006/0063171 A1 | 3/2006 | Akeson et al. |
| 2006/0154399 A1 | 7/2006 | Sauer et al. |
| 2006/0269483 A1 | 11/2006 | Austin et al. |
| 2006/0287833 A1 | 12/2006 | Yakhini |
| 2007/0020772 A1 | 1/2007 | Cao et al. |
| 2007/0039920 A1 | 2/2007 | Kutchoukov et al. |
| 2007/0042366 A1 | 2/2007 | Ling |
| 2007/0080511 A1 | 4/2007 | Campbell |
| 2007/0084163 A1 | 4/2007 | Lai |
| 2007/0084702 A1 | 4/2007 | Lin et al. |
| 2007/0138132 A1 | 6/2007 | Barth |
| 2007/0178240 A1 | 8/2007 | Yamazaki et al. |
| 2007/0190542 A1 | 8/2007 | Ling et al. |
| 2007/0218471 A1 | 9/2007 | Kim et al. |
| 2007/0231795 A1 | 10/2007 | Su |
| 2007/0238112 A1 | 10/2007 | Sohn et al. |
| 2008/0041733 A1 | 2/2008 | Hibbs et al. |
| 2008/0085840 A1 | 4/2008 | Buzby |
| 2008/0096287 A1 | 4/2008 | Barth |
| 2008/0102504 A1 | 5/2008 | Akeson et al. |
| 2008/0119366 A1 | 5/2008 | Sauer et al. |
| 2008/0171316 A1 | 7/2008 | Golovchenko et al. |
| 2008/0187915 A1 | 8/2008 | Polonsky et al. |
| 2008/0234136 A1 | 9/2008 | Drmanac et al. |
| 2008/0242556 A1 | 10/2008 | Cao et al. |
| 2008/0254995 A1 | 10/2008 | Kim et al. |
| 2009/0005252 A1 | 1/2009 | Drmanac et al. |
| 2009/0011943 A1 | 1/2009 | Drmanac et al. |
| 2009/0035777 A1 | 2/2009 | Kokoris et al. |
| 2009/0099786 A1 | 4/2009 | Oliver et al. |
| 2009/0136948 A1 | 5/2009 | Han et al. |
| 2009/0176652 A1 | 7/2009 | Dahl et al. |
| 2009/0214392 A1 | 8/2009 | Kameoka et al. |
| 2010/0078325 A1 | 4/2010 | Oliver |
| 2010/0243449 A1 | 9/2010 | Oliver |
| 2012/0074925 A1 | 3/2012 | Oliver |

FOREIGN PATENT DOCUMENTS

| | | |
|---|---|---|
| EP | 1486775 | 12/2004 |
| EP | 1685407 | 8/2006 |
| WO | WO-9004652 | 5/1990 |
| WO | WO-9617957 | 6/1996 |
| WO | WO-9835012 | 8/1998 |
| WO | WO-0009757 | 2/2000 |
| WO | WO-0022171 | 4/2000 |
| WO | WO-0079257 A1 | 12/2000 |
| WO | WO-0118246 | 3/2001 |
| WO | WO-0118246 A1 | 3/2001 |
| WO | WO-0137958 | 5/2001 |
| WO | WO-0142782 | 6/2001 |
| WO | WO-0207199 | 1/2002 |
| WO | WO-0250534 | 6/2002 |
| WO | WO-03000920 | 1/2003 |
| WO | WO-03010289 | 2/2003 |
| WO | WO-03079416 | 9/2003 |
| WO | WO-03106693 | 12/2003 |
| WO | WO-2004035211 | 4/2004 |
| WO | WO-2004085609 | 10/2004 |
| WO | WO-2005017025 | 2/2005 |
| WO | WO-2006020775 | 2/2006 |
| WO | WO-2006028508 | 3/2006 |
| WO | WO-2006052882 | 5/2006 |
| WO | WO-2007041621 | 4/2007 |
| WO | WO-2007041621 A2 | 4/2007 |
| WO | WO-2007106509 | 9/2007 |
| WO | WO-2007111924 | 10/2007 |
| WO | WO-2007127327 | 11/2007 |
| WO | WO-2008021488 | 2/2008 |
| WO | WO-2008039579 | 4/2008 |
| WO | WO-2008042018 | 4/2008 |
| WO | WO-2008046923 | 4/2008 |
| WO | WO-2008049021 | 4/2008 |
| WO | WO-2008069973 | 6/2008 |
| WO | WO-2008079169 | 7/2008 |
| WO | WO-2009046094 | 4/2009 |
| WO | WO-2010111605 | 9/2010 |
| WO | WO-2010138136 | 12/2010 |

OTHER PUBLICATIONS

Invitation to Pay Additional Fees and, Where Applicable, Protest Fee & Partial International Search dated Aug. 19, 2010, PCT/US2010/028848, 7 pages.

Alberts, B., et al., (1970) "T4 Bacteriophage Gene 32: A Structural Protein in the Replication and Recombination of DNA," Nature 227:1313-1318.

Amit, B., et al., (1974) "Photosensitive Protecting Groups of Amino Sugars and Their Use in Glycoside Synthesis. 2-Nitrobenzyloxycarbonylamino and 6-Nitroveratryloxycarbonylamino Derivatives," J. Org. Chem. 39:192-196.

Arratia, R., et al., (1989) "Poisson Process Approximation for Repeats in One Sequence and Its Application to Sequencing by Hybridization," Dept. of Mathematics, University of Southern California.

Austin, M., et al., (2004) "Fabrication of 5nm Linewidth and 14 nm Pitch Features by Nanoimprint Lithography," App. Phys. Lett. 84:5299-5301.

Bains, W., et al., (1988) "A Novel Method for Nucleic Acid Sequence Determination," J. theor. Biol. 135:303-307.

Baliga, R., et al., (2001) "Kinetic Consequences of Covalent Linkage of DNA Binding Polyamides," Biochemistry 40:3-8.

Bianco, P., et al., "Interaction of the RecA Protein of *Escherichia coli* with Single-Stranded Oligodeoxyribonucleotides," Nucleic Acids Research vol. 24. No. 24 (1996) 4933-4939.

Buchmueller, K.L., et al., (2005) "Extending the Language of DNA Molecular Recognition by Polyamides: Unexpected Influence of Imidazole and Pyrrole Arrangement on Binding Affinity and Specificity," J. Am. Chem. Soc. 127:742-750.

Buchmueller, K.L., et. al., (2006) "Physical and Structural Basis for the Strong Interactions of the -ImPy- Central Pairing Motif in the Polyamide f-ImPyIm," Biochemistry 45:13551-13565.

Cao, H., et al., (2002) "Fabrication of 10 nm Enclosed Nanofluidic Channels," Applied Physics Letters 81(1): 174-176.

Cao, H., et al., (2002) "Gradient Nanostructures for Interfacing Microfluidics and Nanofluidics," Applied Physics Letters 81:3058-3060.

Chen, C., et al., (1994) "Analogous Organic Synthesis of Small-Compound Libraries: Validation of Combinatorial Chemistry in Small-Molecule Synthesis," J.Am.Chem.Soc. 116:2661-2662.

Chen, P., et al., (2004) "Probing Single DNA Molecule Transport Using Fabricated Nanopores," Nano Letters 4:2293-2298.

Chetverin, A., et al., (1994) "Oligonucleotide Arrays: New Concepts and Possibilities," Bio/Technology 12:1093-1099.

Cox, M. (2007) "Motoring Along with the Bacterial RecA Protein," Nature Reviews—Molecular Cell Biology 9:127-138.

Dervan, P.B. (2001) "Molecular Recognition of DNA by Small Molecules," Bioorg. Med. Chem. 9:2215-2235.

Dervan, P.B., et al., (2003) "Recognition of the DNA minor groove by pyrrole-imidazole polyamides," Curr. Op. Struc. Biol. 13:284-299.

Doss, R.M., et al., (2006) "Programmable Oligomers for Minor Groove DNA Recognition," J. Am. Chem. Soc. 128:9074-9079.

Drmanac, R., et al. (1989) "Sequencing of Megabase Plus DNA by Hybridization: Theory of the Method," Genomics 4:114-128.

Ellervik, U., et al., (2000) "Hydroxybenzamide/Pyrrole Pair Distinguishes T-A from A-T Base Pairs in the Minor Groove of DNA," J. Am. Chem. Soc. 122:9354-9360.

Farkas, Z., et al., (2003) "DNA Uptake Into Nuclei: Numerical and Analytical Results," J. Phys.: Condens. Matter 15:S1767-S1777.

Fechter, E.J., et al., (2005) "Sequence-specific Fluorescence Detection of DNA by Polyamide-Thiazole Orange Conjugates," J. Am. Chem. Soc. 127:16685-16691.

Floreancig, P.E., et al., (2000) "Recognition of the Minor Groove of DNA by Hairpin Polyamides Containing α-Substituted-,β-Amino Acids," J. Am. Chem. Soc. 122:6342-6350.

Fodor, S., et al., (2005) "Light-Directed, Spatially Addressable Parall Chemical Synthesis" Research Article.

Fologea, D., et al., (2005) "Slowing DNA Translocation in a Solid-State Nanopore," *Nano Lett.* 5(9):1734-7.

Frieze, A., et al., (1999) "Optimal Reconstruction of a Sequence From its Probes."

Gerland, U., et al., (2004) "Translocation of Structured Polynucleotides Through Nanopores," Phys. Biol. 1:19-26.

Gracheva, M., et al., (2002) "Simulation of the Electric Response of DNA Translocation through a Semiconductor Nanopore-Capacitor," Nanotechnology 17:622-633 (I).

Guo, L. (2004) "Recent Progress in Nanoimprint Technology and its Application," J. Phys. D: Appl. Phys 37:R123-R141 (Appendices B-D).

Gygi, M.P., et al., (2002) "Use of fluorescent sequence-specific polyamides to discriminate human chromosomes by microscopy and flow cytometry," Nucleic Acids Research 30:2790-2799.

Halby, L., et al., (2005) "Functionalized head-to-head hairpin polyamides: Synthesis, double-stranded DNA-binding activity and affinity," Bioorg. Med. Chem. Lett. 15:3720-3724.

Heller, C., (2001) "Principles of DNA Separation with Capillary Electrophoresis," Electrophoresis 22:629-643.

Heng, J., et al., (2004) "Sizing DNA Using a Nanometer-Diameter Pore," Biophysical Journal 87:2905-2911.

Hudson, B., (1999) "An Experimental Study of SBH with Gapped Probes."

Jonsson, U., et al., (1991) "Real-Time Biospecific Interaction Analysis Using Surface Plasmon Resonance and a Sensor Chip Technology," BioTechniques, 11:620-627.

Kalaugher, L., (2002) "Diffraction Gradient Lithography Aids Nanofluidics," Nanotechweb.org.

Kanehisa, L. (1984) "Use of Statistical Criteria for Screening Potential Homologies in Nucleic Acid Sequences," IRL Press Limited, Nucleic Acids Research 12:203-213.

Khrapko, K.R., et al., (1989) "An Oligonucleotide Hybridizatioin Approach to DNA Sequencing," FEBS Lett. 256:118-22.

Kim, C., et al., (1992) "Binding Properties of Replication Protein A from Human and Yeast Cells," Mol. and Cell. Bio. 12(7):3050-3059.

Liang, X., et al., (2007) "Single Sub-20 nm wide Centimeter-Long NanoPluidic Channel Fabricated by Novel Nanoimprint Mold Fabrication and Divest Imprinting," Nano Letters 7:3774-3780.

Liang, X., et al., (2008) "Nanogap Detector Inside Nanopluidic Channel for Past Real Time Label-Free DNA Analysis," Nano Letters 8:1472-76.

Loakes, D., et al., (1994) "5-Nitroindole as an Universal Base Analogue," Nucleic Acids Research 22:4039-4043.

Loakes, D., et al., (1995) "3-Nitropyrrole and 5-Nitroindole as Universal Bases in Primers for DNA Sequencing and PCR," 23:2361-2366.

Lohman, T., et al., (1994) "*Escherichia coli* Single-Stranded DNA-Binding Protein: Multiple DNA-Binding Modes and Cooperatives," Annu. Rev. Biochem. 63:527-70.

Lysov, Y.P., et al., (1988) "Determination of the Nucleotide Sequence of DNA Using Hybridization with Oligonucleotides. A New Method" Dokl. Acad. Nauk SSSR 303:1508-1511 [Article in Russian].

Marques, M.A., et al., (2004) "Expanding the Repertoire of Heterocycle Ring Pairs for Programmable Minor Groove DNA Recognition," J. Am. Chem. Soc. 126:10339-10349.

McEntee, K., et al., (1981) "Binding of the recA Protein of *Escherichia coli* to Single- and Double-Stranded DNA," The Journal of Biological Chemistry 266(16):8835-8844.

Meller, A., et al., (2000) "Rapid Nanopore Discrimination Between Single Polynucleotide Molecules," PNAS 97:1079-1084.

Nice, E., et al., (1993) "Mapping of the Antibody- and Receptor-Binding Domains of Granulocyte Colony-Stimulating Factor Using an Optical Biosensor," Journal of Chromatography 646:159-168.

Nichols, R., et al., (1994) "A Universal Nucleoside for Use at Ambiguous Sites in DNA Primers," 369:492-493.

Novopashina, D.S., et al., (2005) "Sequence-Specific Conjugates of Oligo(2'-O-methylribonucleotides) and Hairpin Oligocarboxamide Minor-Groove Binders: Design, Synthesis, and Binding Studies with Double-Stranded DNA," Chemistry & Biodiversity 2:936-952.

Perry, J., et al., (2005) "Review of Fabrication of Nanochannels for Single Phase Liquid Flow," 3rd Intl. Conference on Microchannels and Minichannels, Paper No. ICMM2005-75104.

Pevzner, P. et al., (1991) "Improved Chips for Sequencing by Hybridization," Journal of Biomolecular Structure & Dynamics 9:399-410.

Pevzner, P., (1989) "1-Tuple DNA Sequencing: Computer Analysis," Journal of Biomolecular Structure & Dynamics 7:63-73.

Powell, M., et al., (1993) "Characetrization of the Pf3 Single-Strand DNA Binding Protein by Circular Dichroism Spectroscopy," Biochemistry 32:12538-12547.

Preparata, F., et al., (1999) "On the Power of Universal Bases in Sequencing by Hybridization."

Preparata, F.P., et. al., (2000) "Sequencing-by-Hybridization at the Information-Theory Bound: An Optimal Algorythm," J. Comp. Biol. 7: 621-630.

Robertson, J., et al., (2007) "Single-Molecule Mass Spectrometry in Solution Using a Solitary Nanopore," PNAS, 104:8207-8211.

Rucker, V.C., et al., (2003) "Sequence Specific Fluorescence Detection of Double Strand DNA," J. Am. Chem. Soc. 125:1195-1202.

Sanger, F. et al., (1977) "DNA Sequencing with Chain-Terminating Inhibitors," Proc. Natl. Acad. Sci. USA 12:5463-5467.

Search Report and Written Opinion dated Feb. 5, 2009, PCT/US08/078432.

Shinohara. Y., et al., (1995) "Use of a Biosensor Based on Surface Plasmon Resonance and Biotinyl Glycans for Analysis of Sugar Binding Specificities of Lectins," J. Biochem 117:1076-1082.

Singer, E. (2008) "The $100 Genome," Technology Review.

Smeets, R., et al., (2008) "Translocation of RecA-Coated Double-Stranded DNA through Solid-State Nanopores," Nano Letters.

Southern, E.M. (1996) "DNA Chips: Analysing Sequence by Hubridization to Oligonucleotide on a Large Scale," Trends in Genetics 12(3):110-115.

Storm, A., et al., (2005) "Fast DNA Translocation through a Solid-State Nanopore," Nano Letters 5(7):1193-1197.

Strezoska, Z., et al., (1991) "DNA Sequencing by Hybridization: 100 Bases Read by a Non-Gel-Based Method," Proc. Natl. Acad. Sci. USA 88:10089-10093.

Tegenfeldt, J., et al., (2004) "The Dynamics of Genomic-Length DNA Molecules in 100 nm Channels," Proc. Nat. Acad. Sci. USA 101:10979-10983.

Terwilliger, T., et al., (1996) "Gene V Protein Dimerization and Cooperativity of Binding to Poly(dA)," Biochemistry 35:16652-16664.

Tucker, P., et al., (1994) "Crystal Structure of the Adenovirus DNA Binding Protein a Hook-On Model for Cooperative DNA Binding," The EMBO Journal 13(13):2994-3002.

Urbach, A.R., (2001) "Toward rules for 1:1 polyamide:DNA recognition," PNAS. 98:4343-4348.

Warren, C.L., et al., (2006) "Defining the sequence-recognition profile of DNA-binding molecules," PNAS. 103:867-872.

Warren, S., (1996) "The Expanding World of Trinucleotide Repeats," Science 271:1374-1375.

Web article (2003) "DNA Combed Into Nanochannels," http://www.nature.com.

Written Opinion dated Jul. 1, 2008, PCT/US06/38748.

Zhang, W., et al., (2006) "Discrimination of Hairpin Polyamides with an αSubstituted-y-aminobutyric Acid as a 5'-TG-3' Reader in DNA Minor Groove," J. Am. Chem. Soc. 128:8766-8776.

Zwolak, M., et al., (2008) Rev. Mod. Phy. 80:141-165 (J).

Akeson, et al., "Microsecond time-scale discrimination among polycytidylic acid, polyadenylic acid, and polyuridylic acid as homopolymers or as segments within single RNA molecules," Biophys. J. 77, 3227-3233 (1999).

Ashkin, "Optical trapping and manipulation of neutral particles using lasers," Proc. Natl. Acad. Sci. USA, vol. 94, DD. 4853-4860, May 1997.

International Search Report for PCT/US04/04138, mailed May 4, 2006, 5 pages.

International Search Report and Written Opinion for PCT/US09/558876 dated Feb. 10, 2010.

International Search Report and Written Opinion dated Mar. 24, 2010 for PCT/US09/055878, 13 pages.

Kuo, et al., "Hybrid three-dimensional nanofluidic/microfluidic devices using molecular gates," Sensors and Actuators A, vol. 102 (Oct. 2002):223-233.

Langa, "Self-organized growth of single crystals of nanopores," Applied Physics Letters, AIP, American Institute of Physics, 2003, vol. 82, No. 2, pp. 278-280.

Li et al., "Lon-beam sculpting at nanometre length scales", Nature 412,166-169 (2001).

Losi, et al., "Time-Resolved Absorption and Photothermal Measurements with Recombinant Sensory Rhodopsin II from Natronobacterium pharaonis," Biophys. J. 77, 3277-3286, Dec. 1999.

Meller, et al., "Voltage-driven DNA translocations through a nanopore," Phys. Rev. Lett. 86(15),3435-3438 (2001).

Optical Tweezers: Introduction to Optical Tweezers, Retrieved Apr. 21, 2010 from http://www.nbi.dk/~tweezer/introduction.htm, pp. 1-5.

Partial International Search Report dated Feb. 15, 2010 for PCT/US09/055878, 3 pages.

Storm, et al., "Fabrication of solid-state nanopores with single-nanometre precision," Nature Materials 2,537-540, Aug. 2003.

Tersoff, "Less is more," Nature 412, 135-136, Jul. 2001.

International Search Report and Written Opinion dated Sep. 30, 2010, PCT/US2010/028848, 14 pgs.

Ben-Dor et al, "On the Complexity of Positional Sequencing by Hybridization", Journal of Computational Biology, vol. 8, No. 4, 2001, pp. 361-371.

Branton, Daniel et al, "The potential and challenges of anopore sequencing," Nature Biotechnology, vol. 26, No. 10, Oct. 2008, pp. 1146-1153.

International Search Report and Written Opinion, PCT/US2011/059933, dated Apr. 2, 2012.

Bloom, et al, Applications of Numbered Undirected Graphs, Proceedings of the IEEE, vol. 65, No. 4, Apr. 1977, pp. 562-570.

International Preliminary Report on Patentability, Application No. PCT/US2009/055876, issuance of report Mar. 8, 2011, 6 pages.

International Preliminary Report on Patentability, Application No. PCT/US2009/055878 issuance of report Nov. 29, 2011, 9 pages.

* cited by examiner

BIOPOLYMER SEQUENCING BY HYBRIDIZATION OF PROBES TO FORM TERNARY COMPLEXES AND VARIABLE RANGE ALIGNMENT

CROSS REFERENCE TO RELATED APPLICATIONS

This application claims the benefit of priority under 35 U.S.C. §119(e) to U.S. Provisional Ser. Nos. 60/976,714, filed on Oct. 1, 2007, and 60/976,739, filed Oct. 1, 2007; the entirety of each application is incorporated herein by reference.

This application also incorporates by reference U.S. patent application Ser. No. 11/538,189 entitled "HYBRIDIZATION ASSISTED NANOPORE SEQUENCING", which was filed Oct. 3, 2006, and published as U.S. Patent Publication No. 2007/0190542. This application also incorporates by reference U.S. Patent Application Ser. No. 61/093,885 entitled, "USE OF LATERALLY DISPLACED TRANSVERSE NANOSCALE ELECTRODES FOR VOLTAGE SENSING OF BIOMOLECULES AND OTHER ANALYTES IN FLUIDIC CHANNELS," by Ling et al., which was filed Sep. 3, 2008.

TECHNICAL FIELD

The present invention relates generally to biopolymer sequencing. More particularly, in certain embodiments, the invention relates to the determination of biopolymer sequence information using sequence-specific probes capable of binding to double-stranded biopolymers. For example, positional information of one or more binding locations of the probes along the target biopolymer molecule is determined and a sequence of the biopolymer is derived based on the positional information.

BACKGROUND

There is great interest in identifying the composition and sequence of various biomolecules, such as human DNA, with accuracy and specificity. Sequencing technology, however, is time consuming and expensive to develop and implement. For example, sequencing the DNA of a single individual for the Human Genome Project required over $3 billion of funding.

It is estimated that each person's DNA varies from one another by approximately 1 base in 1000. Knowledge of such genetic variations among human populations may allow the scientific community to identify genetic trends that are related to various medical predispositions, conditions, or diseases, and may lead to the realization of truly personalized medicine where treatments are customized for a given individual based on that individual's DNA. A reduction in the time and cost of DNA sequencing is needed to develop such knowledge and to tailor medical diagnostics and treatments based on the genetic makeup of individual patients.

One particular obstacle inherent in known methods is the inability to accurately position repetitive sequences in DNA fragments. Furthermore, known methods cannot determine the length of tandem short repeats, which are associated with several human genetic diseases.

One emerging sequencing technology employs nanopore or micropore devices. Nanopores are substantially cylindrical holes formed in a membrane or solid media, said holes having diameters that range from about 1 nm to about 200 nm. Some existing methods using nanopores have attempted to detect single DNA bases as they move through a nanopore under a bias voltage. However, it is difficult to detect single DNA bases as each base passes through the nanopore. Furthermore, the use of nanopores small enough to track single stranded DNA are unreliable and difficult to form.

Other methods have attempted to use nanopores to detect DNA hybridization probes or oligonucleotides on a DNA molecule and to recover the DNA sequence information using the method of Sequencing-By-Hybridization (SBH). SBH is a two step procedure, wherein the collection of all subsequences that make up a target sequence is first determined by detecting hybridization of sequence-specific probes or a pool of probes to the target sequence and then using an algorithm that relies on the use of combinatorial methods to reconstruct the full sequence of the target using the collection of subsequences. Most of the SBH methods have relied on standard DNA probes, termed k-mers (see e.g., E. M. Southern. "DNA chips: analysing sequence by hybridization to oligonucleotide on a large scale" *Trends in Genetics,* 12(3), 110-115 (1996)).

SBH procedures can also be used to attach a large set of single-stranded fragments or probes to a substrate to form a sequencing chip. When a solution of labeled, single-stranded target DNA fragments is exposed to the chip, the target fragments hybridize with complementary sequences on the chip. The hybridized fragments can be identified using a radiometric or optical detector depending on the selected label. Each hybridization provides information about whether the fragment sequence is a subsequence of the target DNA. The target DNA can then be sequenced based on which strings are and are not substrings of the target sequence.

The efficiency of SBH methods is poor. For example, large probe arrays are required to sequence modest target lengths. Furthermore, the information regarding the binding position along the target sequence of a given fragment with respect to other fragments is not generated using this experimental approach, and the number of times that a fragment binds a target is also undetermined. While SBH may be a useful for sequencing variants of known molecules, it is not useful for sequencing organic biomolecules at high throughput and accuracy. Still further, the algorithms that are used to reconstruct the target sequence from the hybridization data have not prove useful in practice because known SBH methods do not return sufficient information to sequence long fragments. Thus, these limitations have prevented the adoption of SBH as a primary sequencing method. There is therefore a need for improved methods of sequencing organic biomolecules such as DNA.

SUMMARY

Embodiments of the present invention provide methods for sequencing a biopolymer by forming local ternary complexes along the length of the double-stranded biopolymer target molecule using one or more probes and obtaining information about the location of the probe(s) using a detector. These methods offer particular advantage when implemented with nanopore (including micropore) detection systems.

It is now appreciated that a key problem of analyzing single stranded biopolymers through a nanopore is that single-stranded biopolymers tend to self-hybridize and fold into secondary or higher-order structures. This may prevent entry of the single stranded sequence into the nanopore or stall its migration through the nanopore. Single-stranded DNA has a short persistence length and a measure of the DNA polymer rigidity is at a local level. Thus, folding of single-stranded DNA may falsely provide a signal similar to the presence of a binding probe.

Sequencing organic biopolymers comprising double-stranded DNA has several advantages over the use of single-stranded DNA. Double-stranded DNA, in contrast to single stranded DNA, does not have a tendency to fold into secondary structures, is easier to manipulate prior to the introduction into a nanopore channel, has a consistent transmission speed through nanopore channels, and has a longer persistence length. In addition, higher affinity probe molecules with greater sequence selectivity may be used with double-stranded DNA, than with single-stranded DNA.

In one aspect, the invention features a method for determining a whole or partial sequence of a target biopolymer. The method includes the step of providing a double-stranded biopolymer target molecule. The target molecule (or fragment thereof) is contacted with a first probe or a first collection of probes having specificity for one or more first recognition sites of the target molecule, thereby forming one or more first local ternary complexes along the double-stranded biopolymer target molecule (or fragment thereof), the one or more first recognition sites each having a first known sequence. At least a subset of the one or more first local ternary complexes along the double-stranded biopolymer target molecule (or fragment thereof) is detected to determine a first probe map. The whole or partial sequence of the target biopolymer may be determined using at least the first probe map.

In certain embodiments, the detecting step includes passing the double-stranded biopolymer target molecule (or fragment thereof) through a nanopore and detecting an electrical signal indicative of one or more locations of the one or more local ternary complexes along a length of the double-stranded biopolymer target molecule, thereby determining the first probe map.

The first probe map may include one or more of the following: (a) relative positional information of two or more first local ternary complexes along the double-stranded biopolymer target molecule (or fragment thereof); (b) absolute positional information of one or more first local ternary complexes along the double-stranded biopolymer target molecule (or fragment thereof); and/or (c) error of positional information of one or more first local ternary complexes along the double-stranded biopolymer target molecule (or fragment thereof).

In certain embodiments, the target molecule (or fragment thereof) is contacted with a second probe having specificity for one or more second recognition sites of the target molecule, thereby forming one or more second local ternary complexes along the double-stranded biopolymer target molecule (or fragment thereof), the one or more second recognition sites each having a second known sequence. The detecting step may further include detecting at least a subset of the one or more second local ternary complexes along the double-stranded biopolymer target molecule (or fragment thereof) to determine a second probe map. The determining step may include determining the whole or partial sequence of the target biopolymer using at least the first probe map and the second probe map.

The first probe map and/or the second probe map may include one or more of the following: (a) relative positional information of two or more first local ternary complexes along the double-stranded biopolymer target molecule (or fragment thereof); (b) relative positional information of two or more second local ternary complexes along the double-stranded biopolymer target molecule (or fragment thereof); (c) relative positional information of one or more first local ternary complexes and one or more second local ternary complexes along the double-stranded biopolymer target molecule (or fragment thereof); (d) absolute positional information of one or more first local ternary complexes along the double-stranded biopolymer target molecule (or fragment thereof); (e) absolute positional information of one or more second local ternary complexes along the double-stranded biopolymer target molecule (or fragment thereof); (f) error of positional information of one or more first local ternary complexes along the double-stranded biopolymer target molecule (or fragment thereof); and/or (g) error of positional information of one or more second local ternary complexes along the double-stranded biopolymer target molecule (or fragment thereof).

In certain embodiments, the determining step includes determining a spectrum map from at least the first probe map and the second probe map. Determining the spectrum map may include using a combinatorial sequence reconstruction algorithm. Determining the spectrum map may include determining a candidate sequence by ordering at least two probe sequences using positional information and error of positional information.

The first recognition site sequence and the second recognition site sequence may overlap, and determining the spectrum map may include aligning the recognition site sequences. The first probe may be an n-mer probe, with n being an integer from 3 to 10. The first probe may include one or more moieties, such as a polyamide, a nucleic acid, and/or a peptide nucleic acid. The first probe may include a gapped polyamide molecule.

The contacting step may further include contacting the target molecule (or fragment thereof) with the first probe in the presence of at least one of a recombinational protein or a recombinational enzyme so as to facilitate hybridization of the first probe with the target molecule.

The providing step may include enzymatically synthesizing at least a portion of a second strand upon a single-stranded template. The contacting step may include binding the first probe to a minor groove of the target molecule (or fragment thereof).

The description of elements of the embodiments of other aspects of the invention may be applied to this aspect of the invention as well.

In another aspect, the invention features a method for determining a whole or partial sequence of a target biopolymer. The method includes the step of providing a double-stranded biopolymer target molecule. The target molecule (or fragment thereof) is contacted with a plurality of n probes each having specificity for one or more recognition sites of the target molecule, thereby forming local ternary complexes along the double-stranded biopolymer target molecule (or fragment thereof), each of the recognition sites having a known sequence. At least a subset of the local ternary complexes along the double-stranded biopolymer target molecule (or fragment thereof) is detected to determine one or more probe maps. The whole or partial sequence of the target biopolymer is determined using at least the one or more probe maps.

In certain embodiments, the detecting step includes passing the double-stranded biopolymer target molecule (or fragment thereof) through a nanopore and detecting an electrical signal indicative of locations of the local ternary complexes along a length of the double-stranded biopolymer target molecule, thereby determining the one or more probe maps. The detecting step may be repeated for each of the n probes.

The description of elements of the embodiments of other aspects of the invention may be applied to this aspect of the invention as well.

In yet another aspect, the invention features a method for detecting the sequence of a target nucleic acid. The method includes contacting a target molecule with a first probe to create at least one probe-target complex at a recognition site of the target for which the first probe has a known specificity, while leaving uncomplexed, regions of the target for which the first probe is not specific. The target molecule is contacted with a second probe to create at least one probe-target complex at a recognition site of the target for which the second probe has a known specificity, while leaving uncomplexed, regions of the target for which the second probe is not specific. Complexed and uncomplexed regions of the target are detected and recorded to create a first probe map of the first probe and a second probe map of the second probe, the first probe map and the second probe map incorporating information on the relative position of the hybridization of the probes. A candidate sequence is determined by ordering at least two probe sequences using positional information or a combination of overlapping sequences of the probe molecules and positional information.

One of more of the following features may be included. Detecting the first probe map and detecting the second probe map may be performed sequentially or concurrently.

At least one of the first probe and the second probe may include a tag so as to allow discrimination of bound first probe from bound second probe. The first probe and the second probe may be comprised of mixtures of nucleic acid sequences. Detection may include using a single molecule detector, which may include a nanopore detector.

The description of elements of the embodiments of other aspects of the invention may be applied to this aspect of the invention as well.

In another aspect, the invention features a method for detecting the sequence of a target nucleic acid. The method includes contacting a target molecule with a first probe to create at least one probe-target complex at a recognition site of the target for which the first probe has a known specificity, while leaving uncomplexed, regions of the target for which the first probe is not specific. The target molecule is contacted with a second probe to create at least one probe-target complex at a recognition site of the target for which the second probe has a known specificity, while leaving uncomplexed, regions of the target for which the second probe is not specific. Complexed and uncomplexed regions of the target are detected and recorded to create a first probe map of the first probe and a second probe map of the second probe, the first probe map and the second probe map incorporating information on the relative position of the hybridization of the probes and incorporating information on the error of the positional information for each probe. A candidate sequence is determined by ordering at least two probe sequences using positional information and parameters relating to the error in positional information or a combination of overlapping sequences of the probe molecules and positional information and error in positional information.

One or more of the following features may be included. A parameter relating to error in measured position of a probe may define a range of positions for the probe. The target sequence may be determined by overlapping sequences of at least two probe molecules only when the range of one of the probes overlaps with the range of another probe. The range may be selected so as to be proximal to a sequence position. The range may be different for every probe. Choosing the range further may include using a correlation between the size of the error and the size of the range. Detecting may include using a single molecule detector. The detector may include a nanopore detector.

The description of elements of the embodiments of other aspects of the invention may be applied to this aspect of the invention as well.

In yet another aspect, the invention features a method for determining a sequence of a nucleic acid target. The method includes creating multiple aliquots of a target molecule solution. Each of a plurality of the aliquots is combined and stringently incubated with a different corresponding probe, with each probe-aliquot combination having a plurality of probe molecules having a known specificity for a given subsequence of the target so as to create a probe-target complex for each aliquot. The probes are predominantly complexed with their corresponding subsequences for which they have specificity. The probe-target complexes are detected with a single molecule detector capable of distinguishing regions of the target that are complexed and uncomplexed with the probe so as to generate a probe map that estimates, to within an error, the positions of the multiple instances of the subsequence within the target sequence. The probe maps generated from the multiple aliquots are preliminarily aligned, and a model sequence created that estimates the actual sequence of the target, the model sequence having a growing end. A range of candidate sequences proximal to the growing end are selected from within the set of aligned probe maps. A probe-specific sequence is selected from within the range that has an overlapping region of substantial homology or identity to a sequence at the growing end of the model sequence, yet has at least one base in a non-overlapping region beyond the growing end. At least one base from the non-overlapping region is appended to the growing end.

One or more of the following features may be included. The range may be selected based on at least one estimated probe map positional error. The size of the range may be related to the error. The same range may be used to select sequences from each probe map. A different range may be used to select sequences from each probe map. The detector may be a nanopore detector. Aligning the probe maps from the multiple aliquots may include using at least one of a reference probe, a reference sequence and a reference protein. The target may be fragmented prior to creating the aliquots. Multiple fragment probe maps for a given sequence-specific probe may be aligned and assembled into a target probe map for that probe. The probes may be chosen so as to bind to all possible sequences of DNA. Creating a model sequence may include choosing a starting probe-specific sequence and from a probe map. The multiple probe maps may be aligned in relation to at least one of each other and the target sequence.

The description of elements of the embodiments of other aspects of the invention may be applied to this aspect of the invention as well.

In yet another aspect, the invention features a method for detecting a sequence of a target biopolymer. The method includes providing a double-stranded biopolymer target molecule. The target molecule is contacted with a first probe having a first probe specificity for recognition sites of the target molecule to form a first plurality of local ternary complexes, the first probe having a first predicted recognition site sequence. A detector is used to determine positional information of the first plurality of local ternary complexes.

One or more of the following features may be included. The positional information may include a parameter related to a spatial distance between two local ternary complexes. The target molecule may be contacted with a second probe having a second probe specificity for recognition sites of the target molecule to form a second plurality of local ternary complexes, the second probe having a second predicted recognition site sequence, and a detector may be used to determine positional information of the second plurality of local ternary complexes. The positional information of at least the first and second plurality of local ternary complexes may be aligned to determine a DNA sequence of the target.

The description of elements of the embodiments of other aspects of the invention may be applied to this aspect of the invention as well.

In yet another aspect, the invention features a method for detecting a sequence of a target biopolymer. The method includes providing a double-stranded biopolymer target molecule. The target molecule is contacted with a first probe having a first probe specificity for recognition sites of the target molecule to form a first plurality of local ternary complexes, the first probe having a first predicted recognition site sequence. The target molecule is contacted with a second probe having a second probe specificity for recognition sites of the target molecule to form a second plurality of local ternary complexes, with the second probe having a second predicted recognition site sequence. The formation of the local ternary complexes is detected. A sequence of the target biopolymer is determined by assembling at least the first and second predicted recognition site sequences.

One or more of the following features may be included. Detection may include measuring the relative positions of the local ternary complexes, and/or creating at least one of a probe map or a spectrum map. Assembling may include overlapping the recognition site sequences. One of the first probe and the second probe may include a collection of probe molecules of substantially similar specificity. The probe molecules may include moieties such as polyamides, nucleic acids, and/or peptide nucleic acids. A recombinational enzyme or protein may be added to aid hybridization. Detection may include using a nanopore detector. Providing the double-stranded biopolymer target molecule may include enzymatically synthesizing at least a portion of a second strand upon a single stranded template.

The description of elements of the embodiments of other aspects of the invention may be applied to this aspect of the invention as well.

In yet another aspect, the invention includes a library of probes adapted for determining a sequence of a biopolymer target, the probes may include polyamide molecules. The library may also include gapped polyamide molecules. All of the probes may be gapped polyamides.

The description of elements of the embodiments of other aspects of the invention may be applied to this aspect of the invention as well.

In yet another aspect, the invention includes a method for determining a sequence of an unknown sequence of a biopolymer target. The method includes: (i) contacting the target with a polyamide probe having a specificity for a recognition site of the target; and (ii) detecting whether the probe and target are bound.

One or more of the following features may be included. A predicted sequence of the recognition site may be recorded if the probe is bound. A probe map may be determined. The probe molecule may bind to the minor groove of the target molecule.

The description of elements of the embodiments of other aspects of the invention may be applied to this aspect of the invention as well.

In yet another aspect, the invention includes a method for determining sequence information of a nucleic acid having a sequence. The method includes providing a double-stranded nucleic acid target molecule having a sequence and a plurality of binding sites disposed along the sequence. A plurality of probe molecules having a first sequence specificity are added to the double-stranded nucleic acid target molecule. The probe molecules having the first sequence specificity and the target molecule are incubated so as to effectuate preferential binding of the first probe molecules to both a first binding site and a second binding site of the target molecule. A parameter related to a distance between the first binding site and the second binding site is measured.

A second probe molecule may be added to the double-stranded nucleic acid target molecule, and the second probe molecule and the target molecule may be incubated so as to effectuate preferential binding of the second probe molecule to both a third binding site and a fourth binding site of the target molecule. A parameter related to the distance between the third binding site and the fourth binding site may be measured. The parameter may be measured by passing the target molecule and bound probe molecules through a nanopore.

The description of elements of the embodiments of other aspects of the invention may be applied to this aspect of the invention as well.

BRIEF DESCRIPTION OF THE DRAWINGS

The foregoing features of the invention will be more readily understood by reference to the following detailed description, taken with reference to the accompanying drawings, in which.

DETAILED DESCRIPTION

Figure 1:
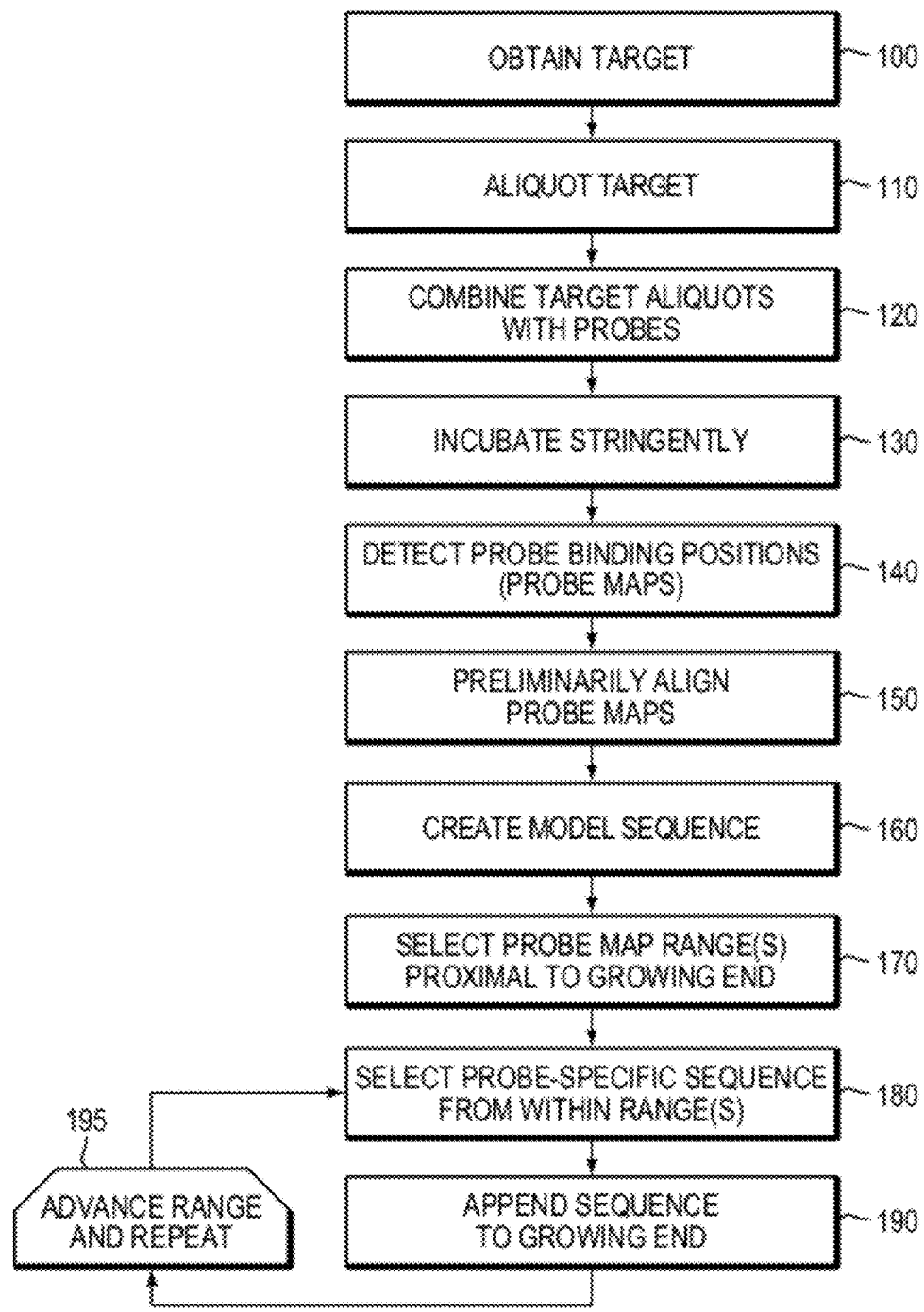
FIG. 1 is a flow chart for a method of sequencing DNA in accordance with an embodiment of the present invention.

As used in this description and the accompanying claims, the following terms shall have the meanings indicated, unless the context otherwise requires:

A "target" means a biopolymer, for example, having sequence information which is to be determined using embodiments of the present invention;

A "probe" means any molecule or assembly of molecules capable of sequence-specific covalent or non-covalent binding to a target molecule;

In connection with a target bound to one or more probes, a "ternary complex" means a complex formed from three or more biomolecules. For example, a complex of two complementary strands of DNA (i.e., double-stranded DNA or dsDNA) with a third probe strand is a ternary complex. Higher order complexes also include ternary complexes; for example, a complex of double-stranded target DNA with two probe molecules bound to the same stretch of sequence, with two probe molecules bound to each other and in turn to a stretch of sequence, with two identical probe molecules bound to different subsequences, or with a probe molecule and a protein bound to a stretch of sequence are quaternary complexes that also include a ternary complex.

A "local ternary complex" means a ternary complex that is localized to a particular stretch of biopolymer. For example, multiple local ternary complexes may exist when probe molecules bind to a target molecule in multiple locations separated by stretches of bases to which the probe is not bound (i.e., uncomplexed regions).

A "polyamide" refers to the class of DNA binding polyamides originally developed by the Dervan laboratory at the California Institute of Technology. Polyamides are molecules containing heterocycle ring structures that can be combined in a modular fashion to recognize DNA sequences by binding in the minor groove of duplex DNA. Typical heterocycle ring structures in this class are, but not limited to, N-methylimidazole, N-methylpyrrole, 3-hydroxy-N-methylpyrrole, N-methylpyrazole, 3-methylthiophene, benzimidazole, hydroxybenzimidazole, imidazopyridine. The rings may be connected via carboxamide linkages, by the amino acid β-alamine, or directly joined by single bonds. Other ring structures and linkages can be envisaged by practitioners familiar with the art.

The polyamides may include spacers that are not sequence specific and that allow the curvature of the polyamide to stay in register with the curvature of double-stranded DNA ("gapped polyamides"). The spacer may be used as a gap when the polyamide is used as a probe for sequence determination. Gapped probes are more efficient at reconstructing sequence information than a non-gapped probe.

In connection with a target and a probe, a "probe map" means a data set containing information related to the sites along a target sequence at which a probe preferentially binds. The data set may include absolute positional information referenced to a known sequence, relative information related to distances between binding sites, or both. The data set may be stored in computer media.

A "spectrum map" means a collection of probe maps determined for a target sequence.

A probe recognition site refers to a target sequence, structure, or conformation that is preferentially recognized by the probe in the presence of other target sequences, structures, or conformations. The probe may interact with the recognition site through non-covalent, covalent, or mixtures of covalent and non-covalent interactions.

In connection with a probe map or a spectrum map, "dynamically weighted spectrum" means the collection of probes under consideration for the extension of a growing sequence with weights as to the likelihood that they should be chosen next. These weights will be based on a parameter related to the measured positions of the probes. The dynamically weighted spectrum may or may not include sequence information. For example, in the case of six-mers, if the growing sequence ends in ATACG, the dynamically weighted spectrum may include only the probes ATACGA, ATACGC, ATACGG, and ATACGT with weights based on their (relative) positions. Alternatively, the dynamically weighted spectrum may be thought of as a collection of probes, independent of sequence, whose probability of being next in the sequence is based on their measured distances from the current growing end of the strand. (In this case sequence-specific information would be incorporated subsequently.)

Illustrative embodiments described herein relate to detecting and analyzing probe maps, to gather sequence information. More particularly, illustrative embodiments described herein relate to creating and detecting specific ternary complexes along double-stranded biopolymer target molecules to gather sequence information. For simplicity, the embodiments described below use DNA as a target, but other biopolymers such as RNA may also be sequenced. In an embodiment, probes that are selective for one or more sequences are hybridized to a target sequence. The target sequence may be double-stranded DNA and the probes are chosen for the ability to bind to one or more sites of double-stranded DNA. The binding of the probe is then detected using a nanopore to generate a probe map in computer media. By detecting probe binding at multiple subsequences along the target, a spectrum map may be constructed. Information contained in the spectrum map may then be aligned an assembled into a finished sequence.

Like SBH, positional hybridization sequencing relies on the biochemical hybridization of probes to an unknown target. However, once the biochemical hybridization is substantially complete, a detector that determines the position of hybridization is utilized. In addition to determining the position of hybridization, the detector is capable of counting the number of times a probe hybridizes to the target. The positional information allows a combinatorial sequence reconstruction algorithm to be used that differs from those used in SBH. In standard SBH, the spectrum of the target sequence from which probes are selected during each step of sequence reconstruction includes all the probes that hybridized and this remains constant during the course of the reconstruction. That is, every probe in the spectrum can be used at any step during reconstruction. In the case of positional hybridization detection, the spectrum is a dynamically weighted spectrum. The dynamically weighted spectrum may include all the probes that bound to the target (with different weights). However, in most embodiments the dynamically weighted spectrum will only include a subset of the spectrum. A consequence of not including all the probes is that during reconstruction of the sequence the dynamically weighted spectrum must change at least once in order to encompass all probes in the spectrum.

Other illustrative embodiments relate to methods and computer algorithms for aggregating, aligning and assembling multiple probe maps into a model nucleotide sequence. In a specific embodiment, combinatorial sequence reconstruction algorithm is used to generate spectrum maps for determining sequence information. Due to the complex nature of the calculations and quantity of data generated, it is expected that the methods described herein be carried out in a substantially automated manner by an appropriate computer algorithm running on a computer of adequate speed.

In an illustrative embodiment, detection of local ternary complexes is accomplished by passing double-stranded biopolymer target molecule or fragment thereof through a nanopore and detecting an electrical signal indicative of the locations of the local ternary complexes along the double-stranded biopolymer target molecule. The use of nanopores to detect solution phase DNA hybridization reactions is described in U.S. Pat. No. 6,537,755 to Drmanac, and in U.S. Patent Application Publication No. 20060287833, to Yakhini, both hereby incorporated herein by reference in their entirety.

FIG. 1 shows a flow chart for a method of sequencing a target in accordance with an embodiment of the present invention. For simplicity, this and other embodiments detailed herein use genomic DNA as the target to be sequenced, although other types of molecules, including cDNA, and RNA could be sequenced in this way. A target DNA sequence is extracted from a source and purified (step 100). The starting material may be any of a variety of single or double-stranded nucleic acids, for example, genomic DNA, PCR products, cDNA, RNA-DNA hybrids and the like. The use of double-stranded DNA as a target has several advantages over the use of single stranded DNA. These include a reduction in the amount of secondary structure present in the target strand to be sequenced, a more consistent transmission speed of the DNA through the nanopore, the ability to manipulate single molecules of double-stranded target DNA prior to introduction into the nanopore, a longer persistence length of the DNA, and the use of probe molecules that are of higher affinity and sequence selectivity. While the method may be most powerful with long pieces of DNA to which a probe may bind in multiple subsequence positions, the invention is also applicable to shorter nucleic acids such as viral genomes, plasmids, cosmids etc. The target DNA may be derived from any of multiple sources and may be the genome of an organism whose DNA sequence is unknown, or is known (resequencing). Alternatively, the DNA may be derived from several organisms. The target DNA may be of a known size or range of sizes; alternatively, the size of the target DNA may be unknown. The purification of step 100 may be the complete purification step or performed in conjunction with later steps. For example, a biochip that includes a nanopore may also accomplish further purification via electrophoretic or other methods. Optionally, the target may be amplified by PCR, rolling circle amplification, or other suitable method.

If chromosomal DNA or other large target DNA polymers are to be sequenced, it may be desirable to fragment the DNA. Target DNA may be fragmented by any of a number of commonly used methods including hydrodynamic shearing, sonication, ultrasonic fragmentation, enzymatic cleavage, nebulization, chemical cleavage, and heat induced fragmentation. Hydrodynamic shearing may be favorable if large nucleic acid fragments are desired. A commercially available device, HydroShear (Genomic Solutions, Ann Arbor, Mich., USA), is available that will shear DNA to a tight size distribution. To use this device, double-stranded DNA in solution is passed through a tube with an abrupt constriction. Fluid accelerates to maintain the volumetric flow rate through the smaller area of the constriction. During this acceleration, drag forces stretch the DNA until it snaps. The DNA fragments until the pieces are too short for the shearing forces to break the chemical bonds. The flow rate of the fluid and the size of the constriction determine the final DNA fragment sizes. In one configuration of the device, size ranges of sheared DNA of from 650 base pairs to 40,000 base pairs are achievable. In a second configuration of the device, size ranges of 1,000 base pairs to 9,000 base pairs are achievable.

The target DNA may then be aliquoted (step 110) and combined with probe molecules (step 120). For example, a first aliquot may be combined with a solution containing molecules of probe specific for a first target subsequence (e.g., a 5 to 20 base pair subsequence) and a second aliquot may be combined with a probe that is specific for a second target subsequence. In a simple scheme, the number of aliquots is equal to the number of different probes to be used in the experiment. A single probe (i.e., a collection of probe molecules having the same or functionally equivalent sequence specificity) may then be added to each aliquot of the target DNA. Alternatively, the number of aliquots may be smaller or larger than the number of different probes; a mixture of probes may be added to each aliquot. The probes may be of either uniform or differing lengths. Various mixing procedures may be used to combine the target and probe, but if the procedure is performed at very low volumes (e.g., 0.1-10 nanoliter), diffusional mixing may suffice.

The aliquots are then incubated under stringent conditions (step 130) to allow the probe molecules to sample multiple subsequences and to approach equilibrium in finding energetically favored subsequences to bind to (i.e., the subsequences for which the probe is specific). In other words, each aliquot containing target DNA and a probe or a mixture of probes is incubated under conditions that result in greater hybridization of probes to matched recognition sequences than to sequences containing a mismatch. Taking into account the type of probe used, stringency may be adjusted through temperature, salt concentrations, addition of organic solvents, washing with solutions, electrophoretic washing, or other methods. Optionally, incubated aliquots may be combined prior to analysis, especially if tagged probes are used. The result is a formation of specific local probe-target complexes, which, as described below, may be modeled as a probe map (step 140). In specific embodiments, the probe map includes the relative positional information of the local ternary complexes along the double-stranded biopolymer, the absolute positional information of the local ternary complexes along the double-stranded biopolymer, and error of positional information of the local ternary complexes along the double-stranded biopolymer. In another embodiment, second probe specific for one or more second recognition sites of the target molecule is used to generate a second probe map. In yet another embodiment, two or more probes are used for the detection of local ternary complexes, and for the generation of two or more probe maps.

The collection of hybridized or otherwise bound probes and positions may be used to form a model probe map of the target DNA. The probe map may be used to reconstruct the target DNA sequence. For example, multiple probe maps from probes having a variety of sequence specificities may be aligned and assembled to reconstruct a sequence. In an embodiment, n-mer probes are used (e.g. polynucleotide probes), each probe having a specificity for one of $4^n$ possible DNA sequence combinations. A complete library of $4^n$ n-mer probes may be utilized to give complete target sequence coverage. In illustrative embodiments, n is from 3 to 10.

Since the target was fragmented, the complete probe map will be constructed from data derived from the multiple fragments. The probe map may be assembled by matching the pattern between overlapping regions of multiple fragments to arrive at an aggregated hybridization pattern for a given probe having a given target specificity. The pattern matching routine may include determining the 3'→5' orientation of each hybridization pattern, especially if this has not been determined previously, e.g. by comparison to a known sequence in a resequencing operation.

The sequence specificity of a probe, combined with its estimated probe map with respect to the target yields a partial sequence model of the target. In other words, if a probe-target complex is detected, it may be expected that the target sequence contains the subsequence for which a given probe is specific. For sufficiently short probes, this subsequence will likely be repeated multiple times in the target at positions corresponding to the positional information that should be available from detection of binding of that probe. The subsequences may be assigned relative positional information by making use of the distances of measured uncomplexed regions intervening between the probe binding sites.

The positional information will likely contain some error however.

The model sequences derived from the probe map of multiple probes having multiple corresponding sequence specificities may be preliminarily aligned with respect to each other and/or with respect to other landmarks (step 150). For example, for resequencing operations, the sequences may be aligned based on a maximal overlap with a known sequence. Alternatively, the model sequences may be aligned based on maximal overlap with each other or with respect to bound proteins (e.g. zinc finger proteins) included in the mixture, or with respect to other sequence landmarks.

A starting model sequence is created (step 160). For example, a starting sequence may be created using the known sequence specificity of one of the probes for which a probe map has been determined. The chosen probe may be located at or near the 3' or 5' terminus of the preliminarily aligned spectrum map. A growing-end may be chosen for the starting sequence, on the internal side.

In certain embodiments, a spectrum map is generated from at least a first probe map and a second probe map. Determining the spectrum map may include using a combinatorial sequence reconstruction algorithm. Determining the spectrum map may also include determining a candidate sequence by ordering at least two probe sequences using positional information and error of positional information. If the first recognition site sequence and the second recognition site sequence overlap, determining the spectrum map may include aligning the recognition site sequences.

A weighted spectrum is chosen as a subset of the spectrum map with respect to the growing end (step 170). The probes encompassed in this subset of the spectrum are selected using positional information or some parameter related to positional information generated during the detection step. The various sequences corresponding to the probe-specificities for the probes for which binding events were detected within the weighted spectrum are then compared with a sequence of the growing end (in the initial stages of the process, this may be the entire starting sequence). If possible, a sequence is chosen that has maximal identity for the growing end yet extends at least one nucleotide beyond the growing end (step 180). At least one base of the non-overlapping sequence is then appended to the growing end (step 190). The weighted spectrum may then be changed. This process of selecting nucleotides, appending nucleotides, and changing the weighted spectrum is repeated until sufficient sequence is determined or the data set is exhausted (step 195). If more than one nucleotide choice is available for appending, this may be resolved by evaluating each possible choice in terms of maximal overlap for the next few sequence extensions.

Contrastingly, in standard SBH, the weighted spectrum of the target sequence from which probes are selected during each step of sequence reconstruction is exactly equal to the spectrum of the target. That is, every probe in the spectrum can be used at any step during reconstruction. In the case of positional hybridization detection, the weighted spectrum of the target sequence encompassing probes selected during each step of reconstruction may be smaller than the length of the target strand. The weighted spectrum may be as large as the spectrum of the target minus one probe. However, in most embodiments the weighted spectrum will be significantly smaller than the target spectrum. A consequence is that during reconstruction of the sequence, the weighted spectrum must change at least once in order to encompass all probes in the spectrum.

If there were no error in the probe maps with regard to the position of hybridization of the probe, the weighted spectrum could consist of only one probe. Some error is to be expected, however. At the other extreme, if there were no certainty regarding the position of probe locations in a probe map, then the next nucleotide to be appended would logically be selected from any probe binding to the target. This would correspond to standard SBH. Balancing these two extremes, an embodiment of the invention optimizes the weighted spectrum based on estimated error in the positional information contained in each probe map or in the spectrum map. For example, a standard deviation, variance or other quantitative measurement of the error in one or more probe locations may be calculated based on the detector output. The weighted spectrum may then be set to be a multiple of this estimated error. Accordingly, the number of probes encompassed by the weighted spectrum and the size of the error may be inversely proportional, or otherwise inversely correlated. Simply stated, a larger weighted spectrum may be used when a larger positional error is present. The weighted spectrum may be expressed in terms of probes that fall within a fixed number of nucleotides distance from the growing end. Alternatively, the range may vary based on the error in the positional information for each probe, or even based on the estimated error at each probe binding site.

Other alternative calculation methods may be employed including adaptive or genetic algorithms that adjust based on the quality of the sequence output. The output of multiple such methods may also be compared and the best one selected. The range or ranges may be calculated once, multiple times during the procedure, or after each nucleotide is appended.

A number of types of molecules are known to bind in a sequence-specific fashion to double-stranded DNA and may be used as probes in the current invention individually or in combination. The molecules may be composed of one or more moieties such as polyamides, a nucleic acid, and/or a peptide nucleic acid. In a specific embodiment, the molecule is a gapped polyamide molecule such as those described in the following Dervan references: Dervan, P. B. Molecular Recognition of DNA by Small Molecules. *Bioorg. Med. Chem.* 2001, 9, 2215-2235; and Dervan, P. B.; Edelson, B. S. Recognition of the DNA minor groove by pyrrole-imidazole polyamides. *Curr. Op. Struc. Biol.* 2003, 13, 284-299.

Alternatively, the probe molecules may be composed of native or modified DNA oligonucleotides that are capable of binding in a triple stranded fashion with double-stranded DNA. Alternatively, the probe molecules may be nucleic acid molecules that are combined with the target in the presence of a recombinational enzyme or a recombinational protein. A non-limiting example of a useful recombinational enzyme is recA. Further information about binding recA probes to DNA strands is provided in the following two references, incorporated by reference in their entirety herein: Bianco et al., *Nucleic Acids Research* Vol. 24, No. 24 (1996) 4933-4939; and Cox, *Nature Reviews—Molecular Cell Biology*, Vol. 9 (February 2007) 127-138. Alternatively, the molecule may be a peptide nucleic acid capable of binding to double-stranded DNA. Other modified oligonucleotides, proteins, peptides, or other polymers are also capable of binding to double-stranded DNA in a sequence specific fashion and thus may be used.

Figure 2:
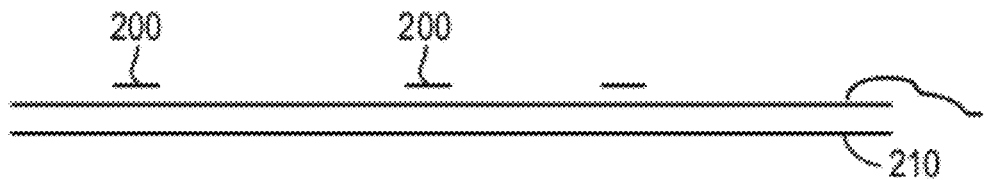
FIG. 2 is a schematic drawing showing a double-stranded DNA target complexed with multiple probe molecules to form local ternary complexes.
Figure 3:
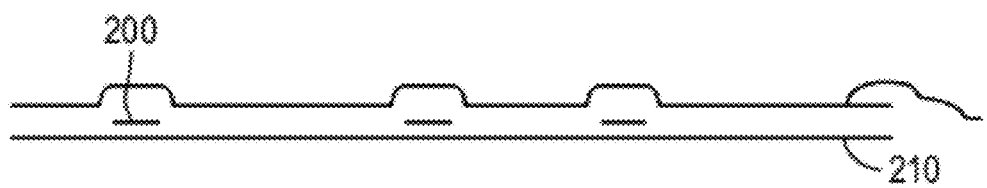
FIG. 3 is a schematic drawing showing a double-stranded DNA target complexed with multiple strand-invading probe molecules to form local ternary complexes.

As shown schematically in FIG. 2, probes 200 will bind to specific subsequences along a DNA strand 210 to create a probe map. In an embodiment, the DNA is double-stranded DNA and the probes may bind to both strands with comparable affinity or preferably to one strand, and may bind to the minor or major groove of helical dsDNA targets. Additionally, as shown in FIG. 3, the probes may invade and disrupt the base pairing of the dsDNA, as is known to occur with certain peptide nucleic acids. In an embodiment, the probes may contain moieties that do not have sequence specific binding behavior. The probe may contain two sequence-specific moieties separated by a relatively non-specific linker moiety. In the case of an oligonucleotide, the non-specific binding region may be composed of a universal base that is able to bind to all four cognate bases (see, e.g., Preparata U.S. Patent Application No. 20010004728.) In the case that the target is double-stranded DNA, the probes may bind to both strands with comparable affinity or preferably to one strand, and may bind to the minor or major groove of helical dsDNA targets. Additionally, as shown in FIG. 3, the probes may invade and disrupt the base pairing of the dsDNA, as is known to occur with certain peptide nucleic acids. Non-specific linkers may also be included in probes that include binding regions composed of polyamides, peptide nucleic acids, peptides, or proteins. Probes may also be labeled to increase detection sensitivity, or to allow discrimination of different probes having different corresponding sequence specificities.

In an embodiment, the probes are polyamides that bind in a 2:1 complex with dsDNA in the minor groove of the DNA. Alternatively or in addition, the polyamide may bind to the DNA in a 1:1 complex or in a 2:1 or higher-order complex. In the case of a 2:1 complex, the two polyamides may be separate molecules or may be covalently joined at the ends or in the middle of the molecules to form hairpin polyamides, cyclic polyamides, H-pin motifs, or U-pin motifs. Charged groups may be placed at either end or in the middle of the polyamides in order to change their affinity for target or for other probe molecules. Linkers may be attached between heterocycles in the polyamide to modulate the curvature of the molecule. Curvature modulation may be used to increase the binding affinity of a polyamide to a longer DNA sequence by matching the curvature of the polyamide to the curvature of the DNA molecule. Other linkages and appendages may also be used.

Polyamide probes may consist of imidazole, pyrrole, hydroxy-pyrrole, benzimidazole, and hydroxybenzimidazole heterocycles. The heterocycles may be substituted with alkyl or functional groups in order to modulate their binding to DNA. Other heterocycles may also be used. Pairing rules of polyamides for minor groove recognition of DNA have been described by Dervan (see Dervan, P. B.; Edelson, B. S. Recognition of the DNA minor groove by pyrrole-imidazole polyamides. Curr. Op. Struc. Biol. 2003, 13, 284-299).

Generally, each aliquot of target DNA is subsequently analyzed to detect binding of the probe to the target DNA. In a specific embodiment, a probe map is generated for each probe to give absolute or relative positional information of probe binding sites located on a longer stretch of dsDNA. The probe binding sites are separated by non-binding, uncomplexed regions of the target that have relatively low affinity for the probe. Accordingly, the probe map may include absolute or relative information related to the location and length (e.g., in base pairs) of the uncomplexed regions.

In an embodiment of the invention, a single molecule detector is used to detect probe binding and thus arrive at a probe map. Unlike detectors typically used for SBH, the single molecule detector may determine the number of times that a given probe binds to a target molecule and the absolute or relative binding sites for that probe. For example, a nanopore based detector, a field effect transistor, Coulomb-charging based detector, or scanning-tunneling or force microscope may be used. Multiple such detectors may be used in parallel or in series. Data from multiple detectors may then be aggregated for analysis, including correlation analysis. Each mixture may be independently analyzed. In an embodiment of the technique, a nanopore is used to detect the position of local ternary complexes on the target DNA.

In certain embodiments, a nanopore-based detector detects temporal changes in current as probe-complexed and uncomplexed stretches of double-stranded DNA pass through the pore. As seen for single stranded DNA, the change in current may be positive or negative depending on the concentration of ions in the buffer on either side of the nanopore. The current may increase or decrease while a probe is passing through the pore due to blockade current, tunneling current or other mechanism.

Figure 4A:
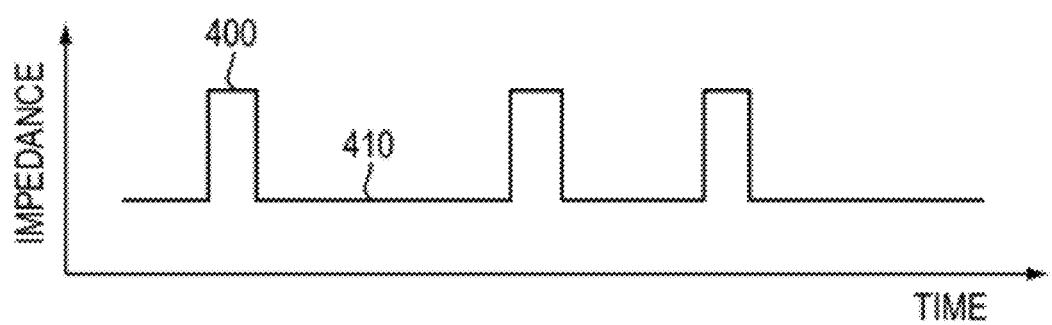
FIG. 4a is a schematic drawing showing an idealized kinetic trace of an impedance measurement generated as local probe-target complexes passes through a nanopore.

FIG. 4a shows an idealized trace of a nanopore readout in terms of impedance as a function of time. Each time a probe molecule 200 passes through the nanopore detector, the impedance level increases (i.e., current blockade). Accordingly, the nanopore signal may be elevated or depressed for a period of time that reflects the length of the probe-target complex (item 400), or the length of the intervening non-binding regions (item 410). Relevant readout information may be recorded on computer media for future analysis.

A current signal, reflecting a change in impedance or current measured by the nanopore detector, may be monitored to gain information about the presence and spacings of hybridized probes. As an analyte moves through a volume monitored by the nanopore detector, the current signal changes. The signal may be elevated or depressed for a period of time that reflects the length of the analyte, e.g., a probe-target complex, or the length of the intervening regions without probes. A typical analyte will impede the flow of ions in the electrolyte and is non-conductive. Therefore, the current typically decreases as the analyte flows through the sensing volume. In some embodiments, e.g., a low salt electrolyte and a charge-carrying analyte, the current signal may increase as the analyte flows through the sensing volume. The current signal further changes when the portion of the analyte containing the hybridized probe moves through the volume between the sensing electrodes.

Figure 4B:
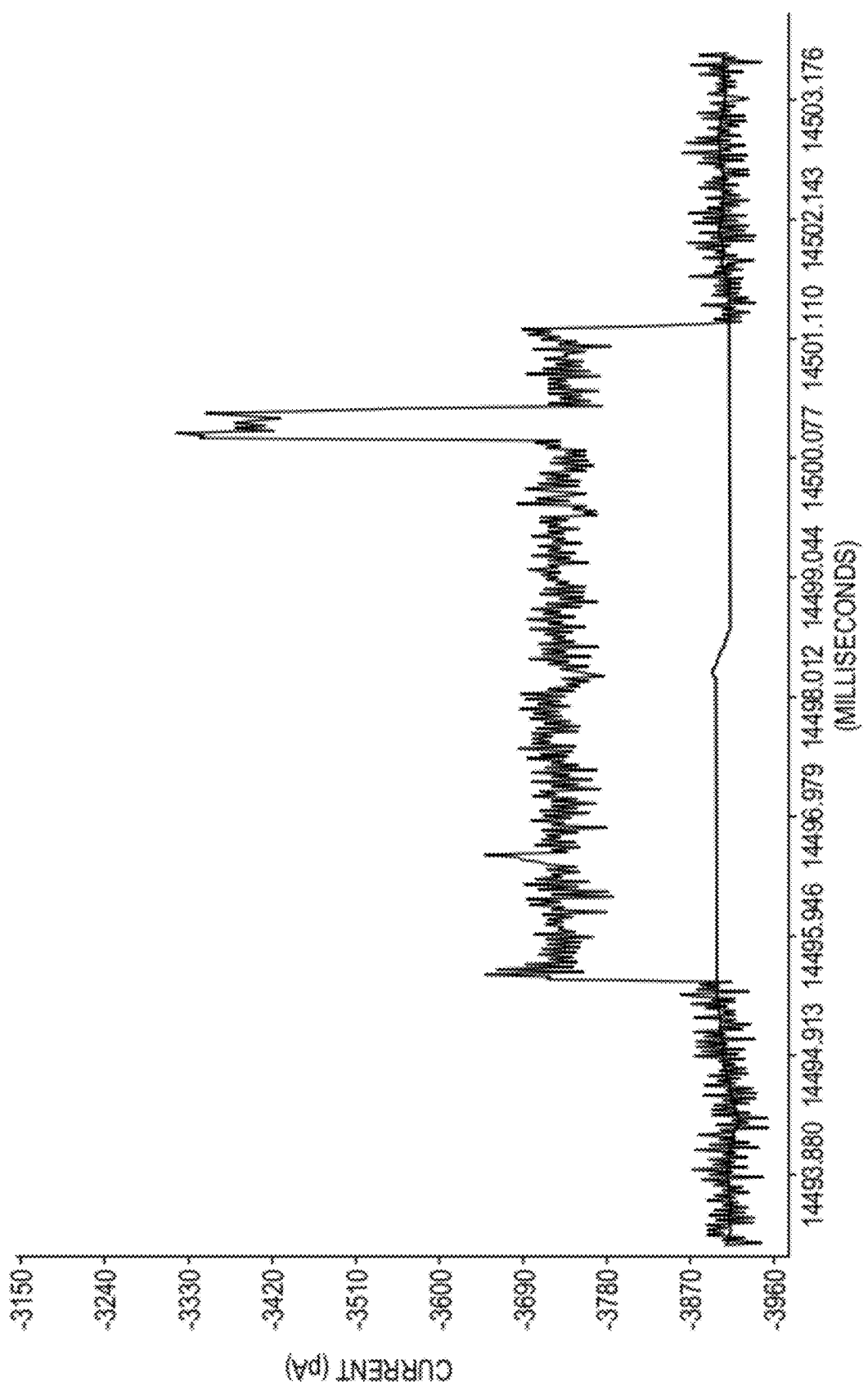
FIGS. 4b and 4c each show a graph of an exemplary current signal determined in accordance with an embodiment of the invention.
Figure 4C:
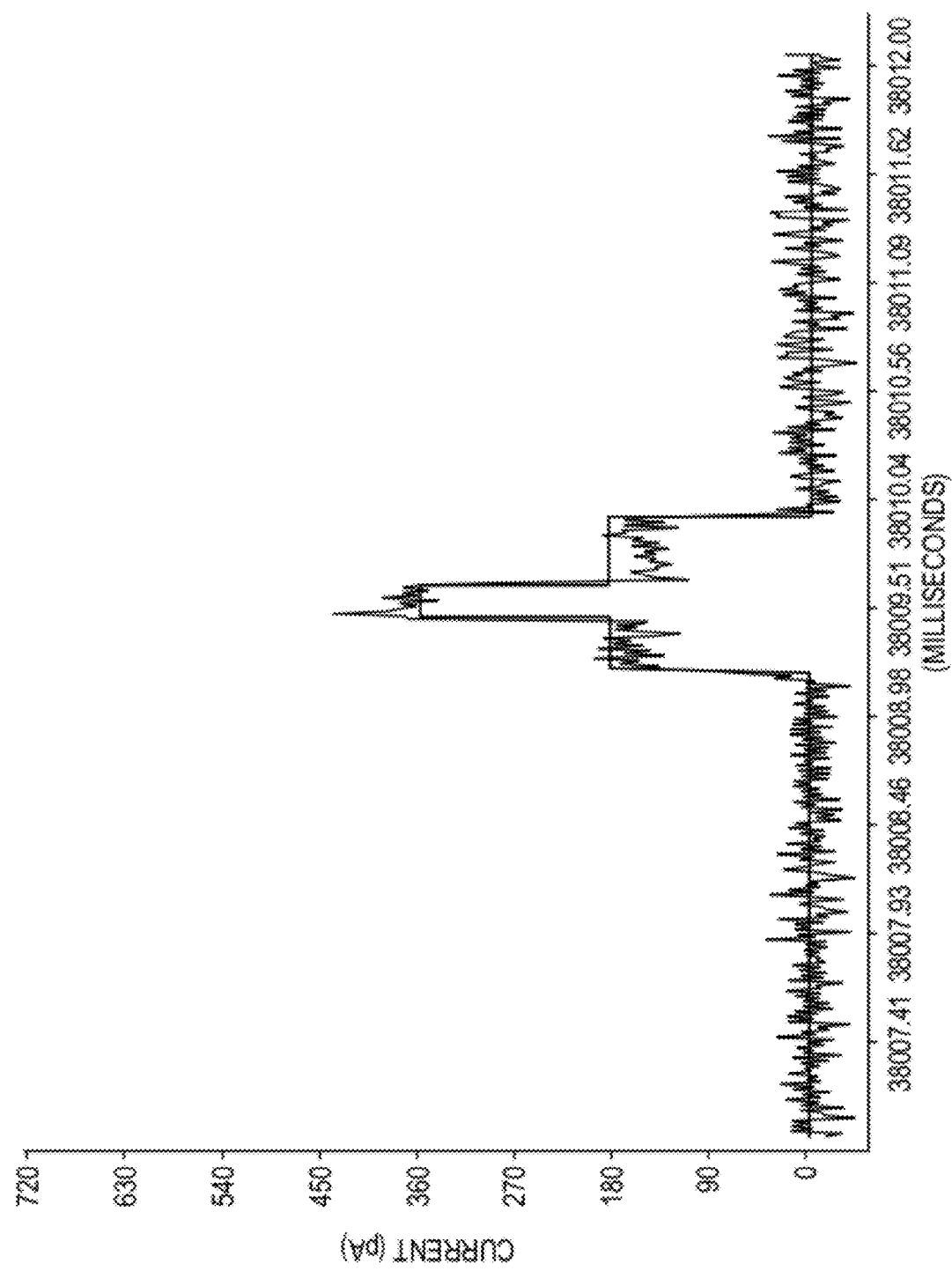

Referring to FIG. 4b, sample data is presented for a piece of double-stranded DNA with an attached probe passing through a pore. The x-axis is time in milliseconds and the vertical axis is current in picoamps. A negative current was run, so that the trace starts at about −3920 pA. That is the current when only buffer is present in the pore. As a DNA strand entered the pore, the current was reduced by almost 200 pA to about −3720 pA. When the section of DNA that had the probe attached passed through the nanopore, there was a further reduction in the current to a little less than −3420 pA. After the DNA and probe passed through, only DNA was in the nanopore, and the current returned to −3720 pA. When the DNA exited the pore, the current returned to the baseline of −3920 pA. FIG. 4b provides similar data, with the application of a baseline correction. Thus, the baseline appears at 0 pA and the peaks indicate the difference between the baseline and the chosen peak height.

A time interval between current signal changes may be recorded. The duration of the change in the current signal may indicate a presence of a hybridized probe. This duration may be used to determine a distance between two probes on the biopolymer. To determine the distance, one may calibrate the system with known standards and calculate an average speed for the analyte in the channel. Time would then be directly related to distance. In embodiments with multiple hybridized probes, multiple peaks may form, with each peak corresponding to a hybridized probe, with the time between peaks being indicative of the relative spacing of the hybridized probes.

Similarly, the duration of a change in the current signal may be used to determine a length of the analyte.

Figure 5A:
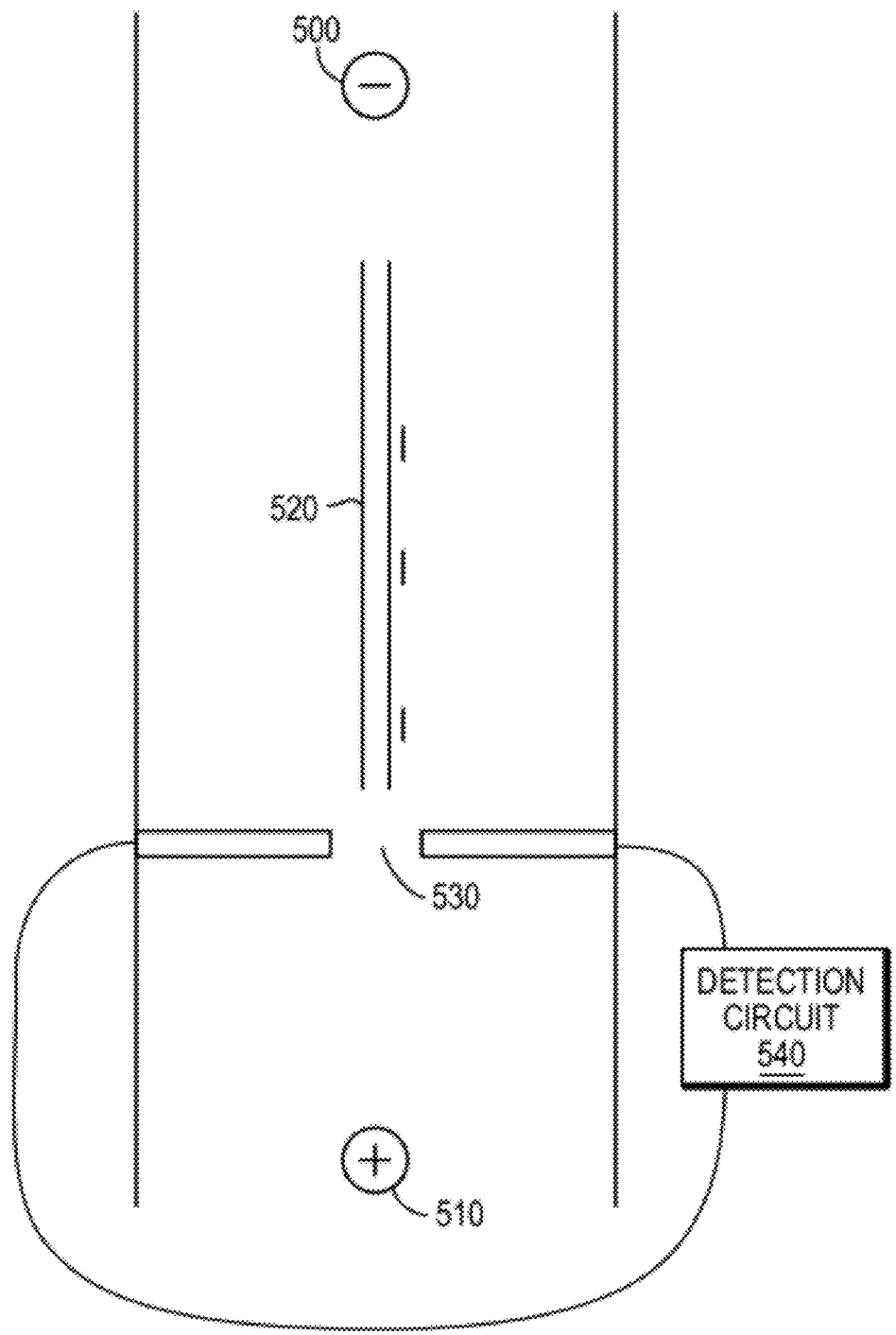
FIG. 5a is a schematic diagram of a nanopore detector in accordance with an embodiment of the invention.
Figure 5B:
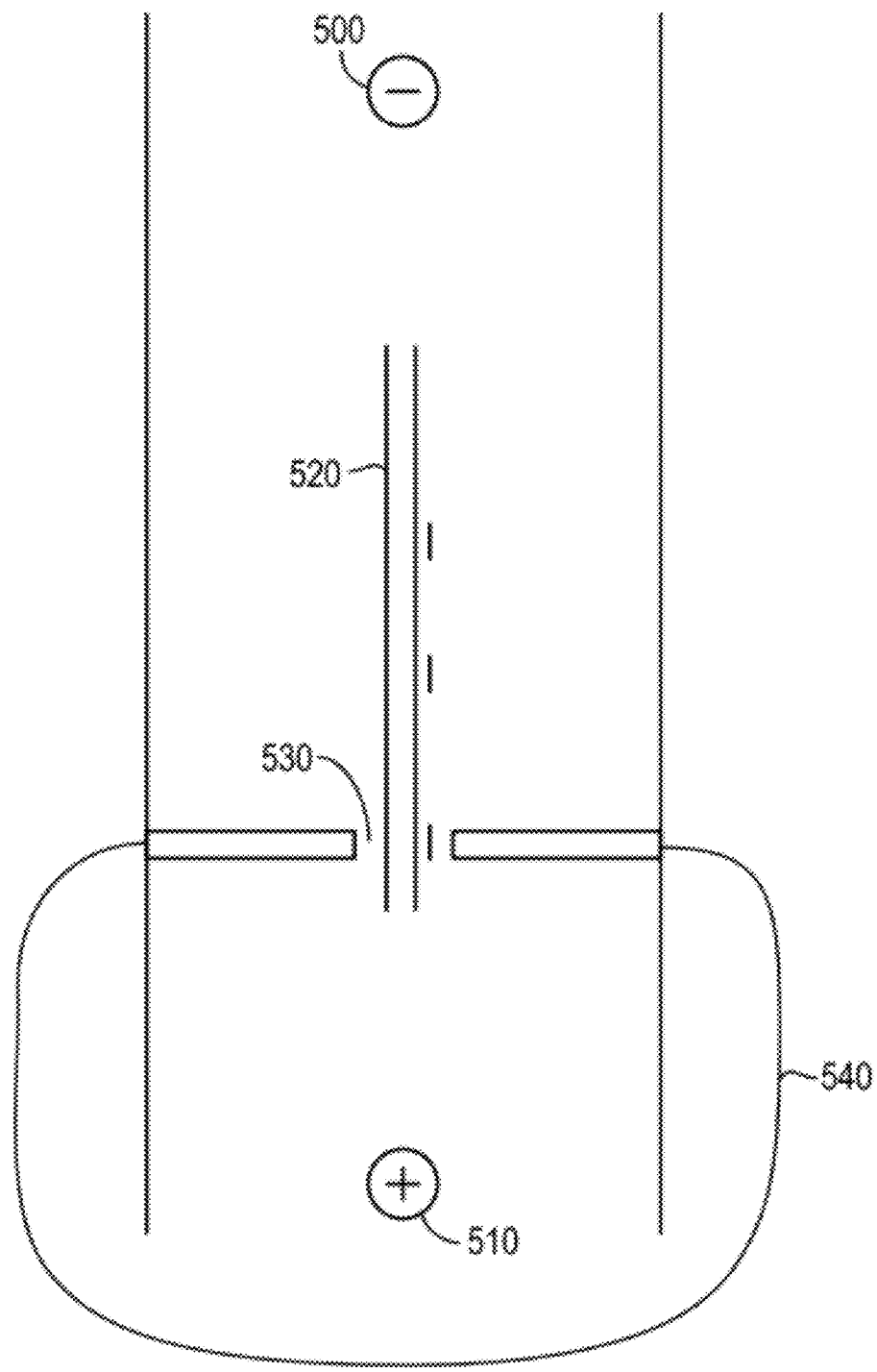
FIG. 5b is a schematic diagram of the detector of FIG. 5a with a local complex within the nanopore in accordance with an embodiment of the invention.
Figure 5C:
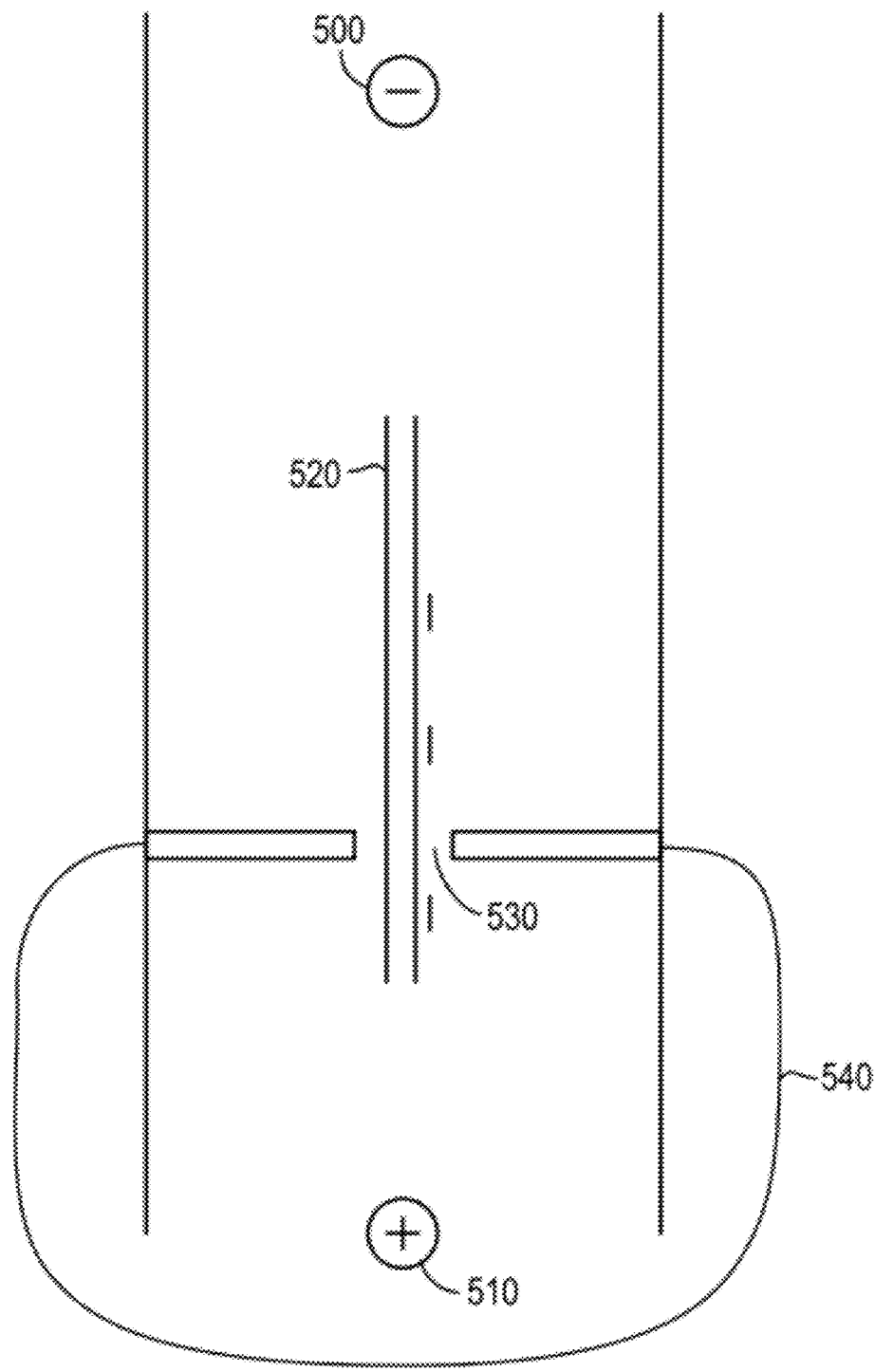
FIG. 5c is a schematic diagram of the detector of FIG. 5a with an uncomplexed region of target DNA within the nanopore in accordance with an embodiment of the invention.

FIGS. 5a-5c schematically show a nanopore detector in accordance with an embodiment of the invention. A cathode 500 and anode 510 (e.g., platinum terminals connected to an appropriate power supply) are positioned to create an electrophoretic field in a buffer solution. The solution is divided into two chambers by a nanopore 530. As a target-probe complex 520 is electrophoretically driven through the nanopore 530 by the electrophoretic field, a detection circuit 540 detects and records positional information related to the location of the bound probes along the length of the target to give a probe spectrum. The target-probe complex is shown as double-stranded, but could be the single stranded complex of FIG. 2. FIG. 5a shows the complex 520 prior to entering the pore 530. FIG. 5b shows the complex 520 within the pore 530; in this state the detection circuit 540 should detect the presence of a bound probe (through an increase or decrease of signal). FIG. 5c shows the complex in a configuration for which the detection circuit 540 should detect the absence of a bound probe. The orientation of the target as it passes through a nanopore may be determined from the probe map, e.g. by comparing the map to a known sequence in a resequencing procedure.

In a related embodiment, the target-probe complex 520 passes through multiple nanopore detectors in sequence. In this way, multiple data sets may be collected and analyzed to give a better signal to noise ratio. This may result in greater accuracy in the probe map. Alternatively, other single molecule detection systems may provide such correlative data.

In a certain embodiment, the biopolymer target molecule is single stranded DNA (ssDNA). Double-stranded DNA may be generated from the single-stranded template by enzymatically synthesizing the second strand and thereby afford may of the aforementioned benefits of using dsDNA: a reduction in the amount of secondary structure present in the target, a more consistent transmission speed of the DNA through the nanopore, the ability to manipulate single molecules of target DNA prior to introduction into the nanopore, and a longer persistence length of the DNA. In an alternative embodiment, ssDNA is stabilized using a plurality of single-stranded DNA binding agents to stabilize the single stranded DNA. The binding agent molecules may be nonspecific, or may be chosen to have specificity for various DNA target subsequences. For example, a mixture of tens, hundreds, or thousands of short (e.g., designed to bind to 6-mers) DNA, or DNA analogs designed to target particular target subsequences may be stringently incubated with a target ssDNA sample. One or more detection probes may then be added and the mixture incubated under stringent conditions. The mixture may be chosen so as to not preclude a detection probe from binding to its complementary subsequence. Different stabilizing agent mixtures may be used with additional aliquots containing target combined with additional detection probes having different subsequence specificity. In related embodiments, the mixtures of stabilizing agents may be chosen to be non-overlapping in their sequence specificity. Using locked nucleic acid or peptide nucleic acid probes may allow the use of more stable probes, capable of binding in higher stringency conditions (e.g., high temperature or low-salt). As a result, the mixture may require fewer agents; e.g., a mixture may be sufficient that binds to only a third or less of the ssDNA sequence.

The reconstruction algorithm, in accordance with some embodiments of the invention, may include the following steps. The reconstruction algorithm proceeds iteratively, adding letters to the reconstructed DNA sequence from 5' to 3'. Progress along the sequence is measured by the variable position, which increases in increments of 1 from 0. The set of available probes is the population of probes whose annealing to the target strand is measured at a position within some distance $\Delta$ of position. Each element in the set of available probes is a Record, an object containing the probe's sequence and the position at which it was measured on the target strand. Let Possibility denote a structure consisting of a string denoting a DNA sequence, a real number score proportional to the logarithm of Possibility's probability, a boolean value sentinel, and a list of Records used by this sequence.

Figure 6:
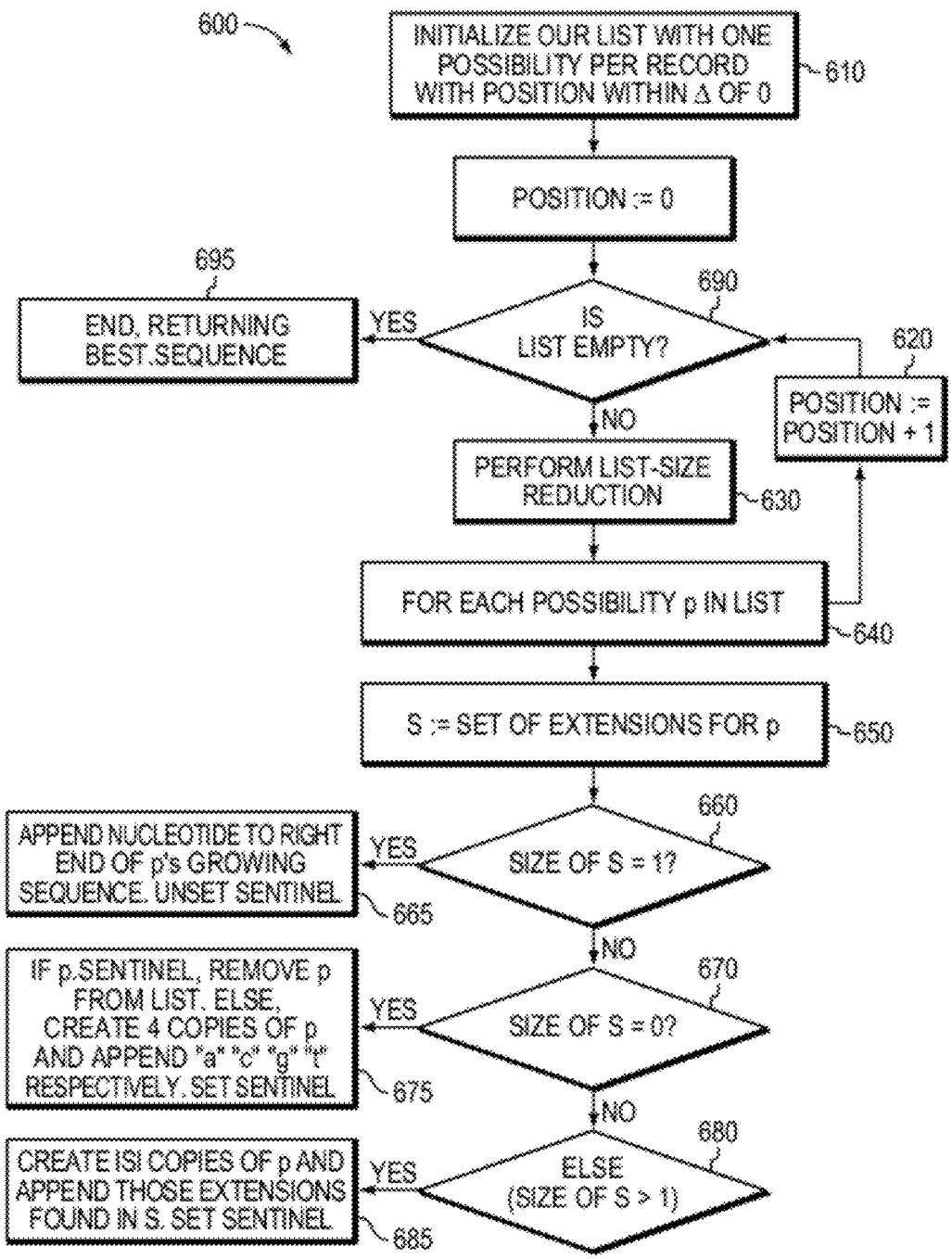
FIG. 6 is a flow chart illustrating a reconstruction algorithm in accordance with an embodiment of the present invention.

Referring to FIG. 6, the algorithm 600 proceeds in three stages: initiation, elongation and termination.

Initiation:
Position is initialized to 0 and a list of Possibilities with one Possibility per Record in the set of available probes about 0 (step 610). The Possibility with Record r is given score of (r.position−0)^2.

Elongation:
Increment position by 1 (step 620).
Trim the list of Possibilities as described below with reference to FIG. 7 (step 630).
For each Possibility p in the list of Possibilities (step 640):
Let S denote the set of Records r in the set of available probes that satisfy the condition that, if l is the length of the probe indicated by r, the l−1-length suffix of the sequence denoted by p is equal to the l−1-length prefix of the probe indicated by r (step 650). (Note that it is not stipulated that all probes are of a length, as discussed in more detail below.) Such a probe sequence is called an extension of p. r is also preferably absent from p's list of Records used, so that each Possibility uses each Record only once. If more than 1 Record in S denotes the same probe-sequence, remove all but the one with the lowest measured position.
If |S|=1 (step 660), let the single Record in S be called r. Append the final character of r's probe to p's DNA sequence, add (r.position−position)^2 to p.score, set p.sentinel to false and add r to the set of Records used by p (step 665).
If |S|=0 (step 670) and p.sentinel=true, remove p from the list of Possibilities and continue. If p.sentinel=false, remove p from the list of Possibilities and add 4 new Possibilities to the list with the DNA sequence and score of p, setting their sentinels to true. Increase the score of each new Possibility by some fixed amount ($\Delta$^2 may be used). This action (extending a sequence without finding a Record to extend it) is called a reach (step 675).
If |S|>1 (step 680), remove p from the list of Possibilities. For each Record r in S, add a new Possibility q which is a copy of p. Append the final character of r's probe to q's DNA sequence, add (r.position−position)^2 to q.score, set q.sentinel to true and add r to the set of Records used by q. This action (extending new sequences according to multiple found Records to extend it) is called a branch (step 685).

Termination:
Eventually, the end of the data set is reached and the set of available probes will be empty (step 690). At this point, the list of Possibilities will decrease in membership until there are no Possibilities left. As Possibilities are removed, a reference is kept to the best Possibility. best is the Possibility whose number of used probes is greatest, measured by position at which the Possibility is terminated minus the number of reaches the Possibility made. If more than one Possibility have used the same number of probes, best is the Possibility with the lowest score. The sequence stored in best is returned as the reconstructed sequence of the target strand (step 695).

Reducing List Size

Figure 7:
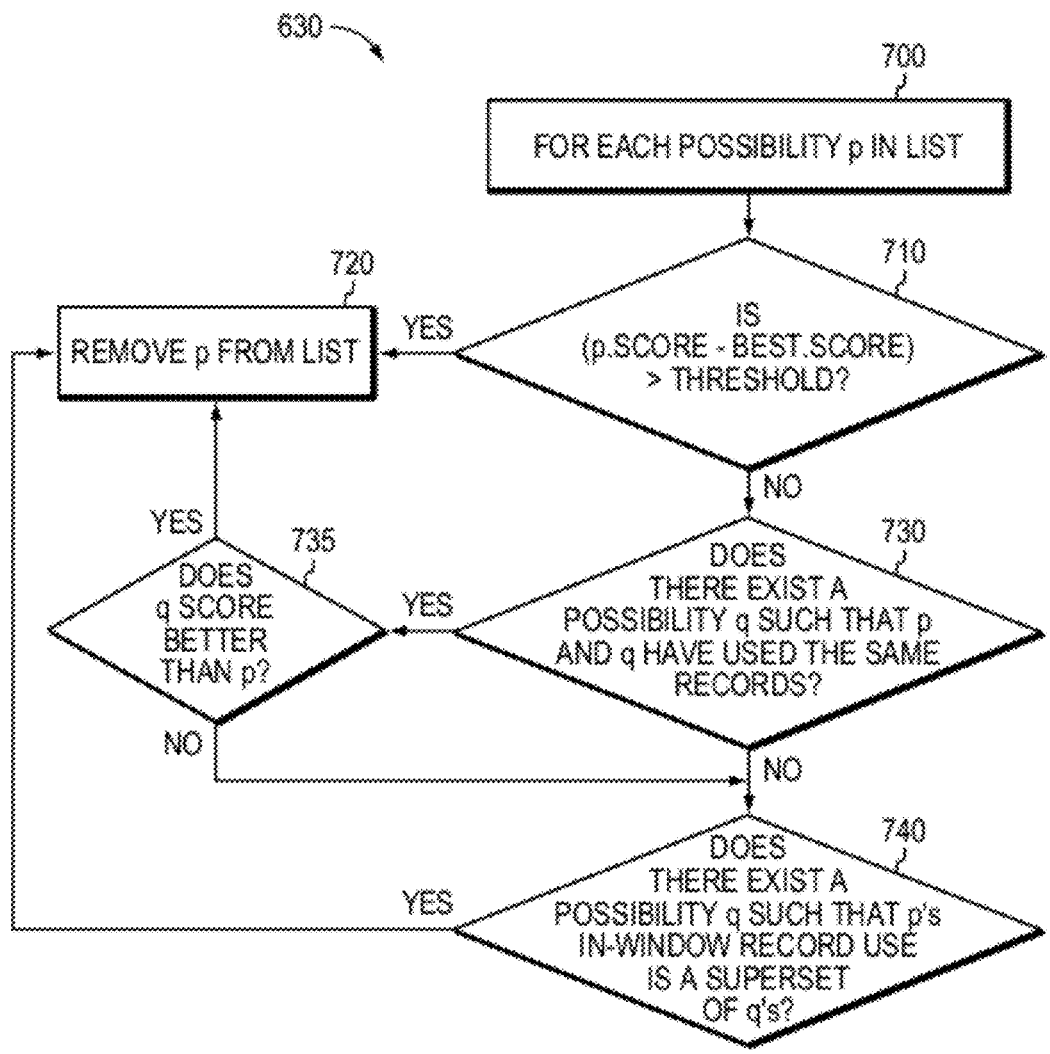
FIG. 7 is a flow chart illustrating an algorithm for reducing possibilities during DNA sequencing in accordance with an embodiment of the present invention.

As described above, the algorithm 600 has exponential runtime because the list of Possibilities grows by a factor of at least one at each position. In practice, the base of this exponent is highly sequence and probe-length-dependent since a branch takes place when two probes with the same prefix are found within a distance of 2Δ. Since exponential runtimes are intractable, it is preferable to keep the size of the list of Possibilities from growing too much. Referring to FIG. 7, at each step, before elongating the putative Possibilities (step 700), the following list-size reducing measures (step 630) are enacted:

A. Haircutting (Step 710)

Since a Possibility's score is proportional to the log-probability of the Possibility, one may impose a lowest probability that one is willing to entertain in a Possibility. All Possibilities in the list whose probabilities are worse than the best-scoring Possibility by a certain amount are removed from the list (step 720).

B. Parallel Culling (Step 730)

A problem with traditional SBH using probes of length k are the so-called SBH failure modes. These modes arise in sequences of the form AbAcA or AcBdAeB, where A and B are sequences of length k–1 and b, c, d and e are sequences of any length. In the first case, it is not possible to distinguish between AbAcA and AcAbA while in the second case, it is not possible to distinguish between AcBdAeB and AeBdAcB. These modes pose a challenge to the disclosed algorithm as well, because each SBH failure mode produces two Possibilities that have used exactly the same probes and now extend the same sequence. Therefore, each SBH failure mode doubles the number of Possibilities in the list. In parallel culling, the complete list of active Possibilities is examined. Any two Possibilities that have used exactly the same Records and are extending the same sequence (i.e. S will be identical when elongation is applied to these Possibilities), are a case of parallel paths. The future, including all reaches and branches of these paths are the same, with the exception that their scores differ by a constant amount. As such, one has all the information one is going to get about the difference in probability between these paths, and one preferably picks the better-scoring option (step 735) and discards the other (step 720). The code is also outfitted to search a reference human genome and eliminate the Possibility whose most recent sequence extensions are not found in the reference. This is effective because, while existing sequencing technologies make large-scale errors, they are generally accurate on the scale in which SBH failure-modes arise in algorithm 600.

C. Jump-Forward Culling (step 740)

Consider two Possibilities p and q that diverged at a branch. Without loss of generality, assume that p is the correct path and that q has been extending incorrect sequence since this branch. Since the re-use of Records is not permitted, the first Record used by q and not by p preferably comes from later on in the sequence and not earlier on. As such, all branches away from the correct path are jump-ahead errors. Let the position at the branch be t and the true position of the first Record used by q after the branch be t+u (true position denotes the position at which the correct path would incorporate the Record). The u probes in between t and t+u remain untouched by q unless q enacts a jump backward to use them. Note that if q makes this jump back and a subsequent jump forward to use all the probes used by p, q and p will have used the same set of probes and one will be in an SBH-failure-mode situation, already handled above. Thus, assume that q does not jump back for these u Records. As such, at any position, q is using a probe whose true position is greater than that of the probe used by p.

Once position increases to the point where all u of the Records skipped by q have positions too low to be in the set of available probes, the set of probes used by q that are in the set of available probes will be a superset of the probes used by p in the set of available probes. Another way of thinking about this is that because q has skipped over u Records and continues to extend the same number of probes asp, q has u fewer Records in its future. The set of Records in the future is the union of the Records whose positions are too high to be in the set of available probes and the set of unused Records in the set of available probes. So having a greater number of used Records inside the set of available probes is identical to having fewer Records available for future use. Since both p and q have used the same number of probes (they are both extending sequences position long) and p has more Records available for future use, p will use more Records in the total and extends a more correct sequence than does q. Therefore, it is safe to remove all Possibilities q from the list for which there exist a Possibility p in the list that uses a subset of the Records still in the set of available possibilities that q does.

Variable Probe-Lengths

In traditional SBH, all probes are of a common length, usually called k. Here, this constraint has been removed as a result of observations about the nature of human DNA. Simulations of DNA sequencing algorithms on random DNA (data strings in which each letter has an independent probability of being "a," "c," "g," or "t") are inevitably more favorable than simulations done on sequences drawn from human DNA. In the case of the disclosed algorithm, this is because short sequences are found repeated in very short stretches. In classical SBH, a repeated element of length k–1 produces a branch-point. In the disclosed approach, this increases the computational burden by doubling the number of Possibilities in the list. It also exposes one to the chance of making incorrect decisions in cutting down the size of the list by Haircutting or Parallel-culling. In random DNA, the probability of finding two Records in the set of available probes with the same k–1-length prefix is equal for all k–1-length prefix strings. In human DNA, however, certain strings are enormously more common. To avoid these ambiguities, longer probes are used for all sequences exhibiting higher frequency.

A. Non-repeated prefixes

Consider the case where the input string has the following form: acatagtctgat (SEQ ID NO: 1) . . . gtatagtctgaa (SEQ ID NO: 2) (where . . . is a sequence of DNA no longer than Δ). One may wish to sequence this string by classical SBH with k=8. The underlined prefix agtctga is found twice, which would introduce a branch in the reconstruction. To avoid this ambiguity, one may extend the probe prefix back until the two are different: (agtctga, agtctga)->(catagtctga (SEQ ID NO: 3), tatagtctga (SEQ ID NO: 4)). Using a probe of length 11 instead of 8 eliminates this branch point and restores unambiguous reconstruction of this sequence. By analyzing existing versions of the human genome, one can develop a collection of proximally-repeated short elements ("ccctccct" is an identified example, as are all of the homopolymer strings) for which to recommend longer probes.

B. Information content

Another approach for probe set design is an examination of the information content of certain probes. In the human genome, there are functionally-relevant regions of reduced alphabet, i.e., regions in which only 2 or 3 of the DNA bases are found. These regions are generally either structural DNA (centromeres, telomeres, constitutive heterochromatin) or DNA that codes for functional RNA. In such regions, all probes exhibit the reduced alphabet of the region, which makes for greater ambiguity. For example, there are $4^7=16,384$ prefixes of length 7 in a region in which the alphabet is all four letters of the DNA alphabet but only $2^7=128$ prefixes of length 7 for a region with alphabet reduced to size 2. Therefore in a region of alphabet of size 2, there are only 128 possible prefixes and a branch event is 128 times as likely as in a 4-alphabet region. To increase the number of prefixes, it is proposed that probes with reduced alphabet be longer. Specifically, if full-alphabet probes of length 8 were used (prefix of length 7), 3-letter-alphabet probes of length 10 would be used ($3^9=19,683\sim16,384$) and 2-letter-alphabet probes of length 15 would be used ($2^{14}=16,384$).

C. Non-Redundant Prefixes

Using probes of variable lengths opens the door for considerable redundancy.

Redundancy is desirable because it permits multiple measurements to cross-check, but it may complicate matters by altering the probability model surrounding a single Record. Specifically, if a single Record represents two probe-landings (one of "aaaaaaaa" and another of "aaaaaaaaa") it should be treated as though it has less error than would a single probe-landing. To avoid these complications and keep the number of reactions down, the following condition may be imposed on any probe set: Let T denote the set of all infinitely-long strings over the alphabet {"a," "c," "g," "t"}. For all strings str in T, there exists exactly one probe p of length l in our probe set such that the l–1-length prefix of p is a suffix of str. This is identical to the condition that no probe in our probe set is the suffix of another.

In certain embodiments, the disclosed methods for biopolymer sequencing are implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Such computer instructions can be written in a number of programming languages for use with many computer architectures or operating systems.

Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Some embodiments of the invention may be implemented as a combination of both software (e.g., a computer program product) and hardware. Still other embodiments of the invention are implemented as entirely hardware, or entirely software (e.g., a computer program product).

In one embodiment, the steps described above are used to determine a whole or partial sequence of a target biopolymer. The method may include providing a double-stranded biopolymer target molecule. Then, the target molecule or fragment thereof may be contacted with a plurality of n probes each having specificity for one or more recognition sites of the target molecule, thereby forming local ternary complexes along the double-stranded biopolymer target molecule or fragment thereof, each of the recognition sites having a known sequence. At least a subset of the local ternary complexes along the double-stranded biopolymer target molecule or fragment thereof may be detected to determine one or more probe maps. A whole or partial sequence of the target biopolymer may be determined using at least one or more probe maps.

Detection may include passing the double-stranded biopolymer target molecule or fragment thereof through a nanopore and detecting an electrical signal indicative of locations of the local ternary complexes along a length of the double-stranded biopolymer target molecule, thereby determining the one or more probe maps. This detection step may be repeated for each of the n probes.

References, patents, and published patent applications specified herein are incorporated herein by reference.

The described embodiments of the invention are intended to be merely exemplary and numerous variations and modifications will be apparent to those skilled in the art. All such variations and modifications are intended to be within the scope of the present invention as defined in the appended claims.

What is claimed is:

1. A method for determining a whole or partial sequence of a target biopolymer, the method comprising the steps of:
providing a double-stranded biopolymer target molecule;
contacting said target molecule or fragment thereof with a first probe having specificity for one or more first recognition sites of said target molecule, thereby forming one or more first local ternary complexes along said double-stranded biopolymer target molecule or fragment thereof, said one or more first recognition sites each having a first known sequence, wherein the first probe is a member selected from the group consisting of an oligonucleotide, a peptide, and a polyamide;
contacting said target molecule or fragment thereof with a second probe having specificity for one or more second recognition sites of said target molecule, thereby forming one or more second local ternary complexes along said double-stranded biopolymer target molecule or fragment thereof, said one or more second recognition sites each having a second known sequence;
passing said double-stranded biopolymer target molecule or fragment thereof through a nanopore or channel;
detecting an electrical signal indicative of one or more locations of at least a subset of said one or more first local ternary complexes along said double-stranded biopolymer target molecule or fragment thereof to determine a first probe map;
detecting an electrical signal indicative of one or more locations of at least a subset of said one or more second local ternary complexes along said double-stranded biopolymer target molecule or fragment thereof to determine a second probe map; and
determining said whole or partial sequence of said target biopolymer using at least said first probe map and said second probe map.

2. The method of claim 1, wherein said first probe map comprises at least one of the following:
(a) relative positional information of two or more first local ternary complexes along said double-stranded biopolymer target molecule or fragment thereof;
(b) absolute positional information of one or more first local ternary complexes along said double-stranded biopolymer target molecule or fragment thereof; or
(c) error of positional information of one or more first local ternary complexes along said double-stranded biopolymer target molecule or fragment thereof.

3. The method of claim 1, wherein at least one of said first probe map or said second probe map comprises one or more of the following:
(a) relative positional information of two or more first local ternary complexes along said double-stranded biopolymer target molecule or fragment thereof;
(b) relative positional information of two or more second local ternary complexes along said double-stranded biopolymer target molecule or fragment thereof;
(c) relative positional information of one or more first local ternary complexes and one or more second local ternary complexes along said double-stranded biopolymer target molecule or fragment thereof;
(d) absolute positional information of one or more first local ternary complexes along said double-stranded biopolymer target molecule or fragment thereof;
(e) absolute positional information of one or more second local ternary complexes along said double-stranded biopolymer target molecule or fragment thereof;
(f) error of positional information of one or more first local ternary complexes along said double-stranded biopolymer target molecule or fragment thereof; or
(g) error of positional information of one or more second local ternary complexes along said double-stranded biopolymer target molecule or fragment thereof.

4. The method of claim 1, wherein said determining step comprises determining a spectrum map from at least said first probe map and said second probe map.

5. The method of claim 4, wherein determining said spectrum map comprises using a combinatorial sequence reconstruction algorithm.

6. The method of claim 4, wherein determining said spectrum map comprises determining a candidate sequence by ordering at least two probe sequences using positional information and error of positional information.

7. The method of claim 4, wherein said first recognition site sequence and said second recognition site sequence overlap, and wherein determining said spectrum map comprises aligning said recognition site sequences.

8. The method of claim 1, wherein the first probe is an n-mer probe, wherein n is an integer from 3 to 10.

9. The method of claim 1, wherein the first probe comprises a gapped polyamide molecule.

10. The method of claim 1, wherein the providing step comprises enzymatically synthesizing at least a portion of a second strand upon a single-stranded template.

11. The method of claim 1, wherein the contacting step comprises binding the first probe to a minor groove of the target molecule or fragment thereof.

12. The method of claim 1, wherein the first probe is a polyamide selected from the group consisting of a pyrrole and an imidazole.

13. The method of claim 12, wherein the first probe is pyrrole or a substituted pyrrole.

14. The method of claim 13, wherein the first probe is a member selected from the group consisting of pyrrole, hydroxyl-pyrrole, N-methylpyrrole, 3-hydroxy-N-methylpyrrole, N-methylpyrazole, and 3-methylthiophene.

15. The method of claim 12, wherein the first probe is imidazole or a substituted imidazole.

16. The method of claim 15, wherein the first probe is a member selected from the group consisting of imidazole, benzimidazole, hydroxybenzimidazole, N-methylimidazole, and imidazopyridine.

17. The method of claim 1, wherein the first probe is a polyamide comprising a molecule containing a heterocyclic ring structure.

18. The method of claim 1, further comprising:
fragmenting the double-stranded biopolymer target molecule prior to performing the contacting steps,
wherein determining said whole or partial sequence of said target biopolymer comprises constructing a probe map by matching a pattern between overlapping regions of multiple fragments to arrive at an aggregated hybridization pattern for each probe.

19. The method of claim 1, wherein a sequence of said first recognition site and a sequence of said second recognition site overlap.

20. The method of claim 1, wherein said first and second contacting steps are performed separately with different copies of the same target molecule.

21. The method of claim 1, wherein the second probe is a member selected from the group consisting of an oligonucleotide, a peptide, and a polyamide.

22. A method for determining a whole or partial sequence of a target biopolymer, the method comprising the steps of:
providing a double-stranded biopolymer target molecule;
contacting said target molecule or fragment thereof with a plurality of n probes each having specificity for one or more recognition sites of said target molecule, thereby forming local ternary complexes along said double-stranded biopolymer target molecule or fragment thereof, each of said recognition sites having a known sequence, wherein each of the n probes is individually a member selected from the group consisting of an oligonucleotide, a peptide, and a polyamide;
detecting at least a subset of said local ternary complexes along said double-stranded biopolymer target molecule or fragment thereof to determine one or more probe maps; and
determining said whole or partial sequence of said target biopolymer using at least said one or more probe maps.

23. The method of claim 22, wherein said detecting step comprises passing said double-stranded biopolymer target molecule or fragment thereof through a nanopore and detecting an electrical signal indicative of locations of said local ternary complexes along a length of said double-stranded biopolymer target molecule, thereby determining said one or more probe maps.

24. The method of claim 23, wherein said detecting step is repeated for each of said n probes.

25. The method of claim 22, wherein at least one of the n probes is a polyamide selected from the group consisting of a pyrrole and an imidazole.

26. The method of claim 25, wherein the at least one n probe is pyrrole or a substituted pyrrole.

27. The method of claim 26, wherein the at least one n probe is a member selected from the group consisting of pyrrole, hydroxyl-pyrrole, N-methylpyrrole, 3-hydroxy-N-methylpyrrole, N-methylpyrazole, and 3-methylthiophene.

28. The method of claim 25, wherein the at least one n probe is imidazole or a substituted imidazole.

29. The method of claim 28, wherein the at least one n probe is a member selected from the group consisting of imidazole, benzimidazole, hydroxybenzimidazole, N-methylimidazole, and imidazopyridine.

30. The method of claim 22, wherein at least one n probe is a polyamide comprising a molecule containing a heterocyclic ring structure.

31. The method of claim 22, further comprising:
fragmenting the double-stranded biopolymer target molecule prior to performing the contacting step.

32. The method of claim 31, wherein determining said whole or partial sequence of said target biopolymer comprises constructing a probe map by matching a pattern between overlapping regions of multiple fragments to arrive at an aggregated hybridization pattern for each probe.

33. The method of claim 22, wherein said contacting step is performed separately for each of said n probes using different copies of the same target molecule.

* * * * *

SEQUENCE LISTING

<160> NUMBER OF SEQ ID NOS: 4

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic oligonucleotide

```
<400> SEQUENCE: 1
acatagtctg at                                                                12

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gtatagtctg aa                                                                12

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
catagtctga                                                                   10

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tatagtctga                                                                   10
```